US005774564A

United States Patent [19]

Eguchi et al.

[11] Patent Number: 5,774,564

[45] Date of Patent: Jun. 30, 1998

[54] ACTIVE CONTROLLER USING LATTICE-TYPE FILTER AND ACTIVE CONTROL METHOD

[75] Inventors: Masaki Eguchi, Uji; Fumio Kokubo, Kitakatsuragi-gun, both of Japan

[73] Assignee: Sharp Kabushiki Kaisha, Osaka, Japan

[21] Appl. No.: 322,147

[22] Filed: Oct. 13, 1994

[30] Foreign Application Priority Data

Oct. 13, 1993 [JP] Japan .................................... 5-255877

[51] Int. Cl.[6] ............................ H03B 29/00; A61F 11/06

[52] U.S. Cl. ................. 381/71.11; 381/94.1; 364/724.19

[58] Field of Search ............... 381/71, 94; 375/229–233, 375/350; 364/724.19

[56] References Cited

U.S. PATENT DOCUMENTS

| | | | |
|---|---|---|---|
| 4,677,677 | 6/1987 | Eriksson . | |
| 5,014,232 | 5/1991 | Andre | 364/724.19 |
| 5,315,621 | 5/1994 | Lucioni et al. | 364/724.19 |
| 5,337,366 | 8/1994 | Eguchi et al. . | |
| 5,426,597 | 6/1995 | Herchen, Jr. et al. | 364/724.19 |
| 5,499,302 | 3/1996 | Nagami et al. | 381/71.11 |
| 5,581,495 | 12/1996 | Adkins et al. | 381/71.11 |

FOREIGN PATENT DOCUMENTS

| | | | |
|---|---|---|---|
| 578212 | 1/1994 | European Pat. Off. . | |
| Wo 89/12360 | 12/1989 | WIPO | 364/724.19 |

OTHER PUBLICATIONS

"Lattice Form Adaptive Recursive Digital Filters: Algorithms and Applications", S. Horvath, Jr., Institute of Applied Physics, IEEE Int'l. Conf. on Circuits & Systems, 1980, pp. 128–133.

"Recursive Lattice Forms for Spectral Estimation and Adaptive Control", B. Friedlaner, IEEE Conf. on Decision and Control, 1980, pp. 466–471.

Eriksson, L.J. "The Selection and Application of an IIR Adaptive Filter for Use in Active Sound Attenuation" IEEE Apr. 1987.

*Primary Examiner*—Curtis Kuntz
*Assistant Examiner*—Xu Mei

[57] ABSTRACT

An active controller suppressing an incoming acoustic wave by active control includes a signal processing unit filtering, an input signal corresponding to the incoming acoustic wave to generate an output signal, an error detecting portion detecting an error between the output signal and a desired response value, and an adapting portion adjusting a filtering characteristic of the signal processing portion according to the input signal, the output signal, and an error signal such that the error is minimized. The signal processing portion includes a non-recursive all zero digital filter filtering an input signal, and a lattice-type multi-stage all pole digital filter further filtering an output signal of the non-recursive all zero digital filter. The adapting portion updates a filter coefficient of the signal processing portion adaptively while clipping an absolute value exceeding one of a filter coefficient of the lattice-type multi-stage all pole digital filter.

21 Claims, 11 Drawing Sheets

51, 53

151, 159

ACTIVE CONTROLLER USING LATTICE-TYPE FILTER AND ACTIVE CONTROL METHOD

BACKGROUND OF THE INVENTION

1. Field of the Invention

The present invention generally relates to an active controller and to an active control method for canceling acoustic noise adaptively, and more particularly, to a configuration of a signal processing circuit used in an active noise controller, an active vibration controller, an echo canceler, an adaptive equalizer, and the like.

2. Description of the Related Art

FIG. 1 is a diagram showing a configuration of a conventional active noise control system. Referring to FIG. 1, the active noise control system includes an input microphone 1 extracting input noise to be canceled or attenuated to generate an input signal X, an error microphone 2 extracting post-processed output noise to generate an error signal E, a control unit 3 carrying out adaptive processing, as described later, based on input noise X and error signal E (e(n)) to provide a silencing signal Y, and a speaker 4 generating an acoustic wave according to silencing signal Y from control unit 3. Input microphone 1 and error microphone 2 are arranged in an acoustic wave guide pipe 5 like a duct transmitting an acoustic wave to be canceled or attenuated. Speaker 4 introduces an acoustic wave only into guide pipe 5. Control unit 3 generates silencing signal (hereinafter referred to as an "output signal") Y from input signal X and error signal E so that error signal E attains the minimum level.

FIG. 2 schematically shows a configuration of control unit 3 shown in FIG. 1. Referring to FIG. 2, control unit 3 includes a noise detecting portion 10 converting incoming acoustic wave signal X into a digital input signal x(n), a signal processing unit 20 applying filtering processing, as described in detail later, to input signal x(n) from detecting portion 10 to generate an output signal y(n), a sound wave generating portion 30 converting output signal y(n) from signal processing portion 20 into an analog signal to generate silencing signal Y and to superimpose a sound wave corresponding to silencing signal Y on the incoming acoustic wave, an error detecting portion 40 receiving the sound wave from sound wave generating portion 30 and the incoming acoustic wave (hereinafter referred to as "input noise") to generate error signal e(n), an adapting portion 50 adjusting the processing contents (filter coefficients) of signal processing portion 20 according to output signal y(n) from signal processing portion 20, error signal e(n) from error detecting portion 40, and input signal x(n) from noise detecting portion 10, so that error signal e(n) attains the minimum level. Here, n represents time.

Noise detecting portion 10 includes input microphone 1, an amplifier 11 amplifying a signal from input microphone 1, a low pass filter (LPF) 12 passing only a predetermined low frequency component of an output signal of amplifier 11, and an analog/digital (A/D) converter 13 sampling an output signal of low pass filter 12 at a predetermined time interval to convert the output signal into a digital signal. Low pass filter 12 serves to remove an aliasing caused upon A/D conversion.

Sound wave generating portion 30 includes a digital/analog (D/A) converter 31 converting output signal y(n) from signal processing unit 20 into an analog signal, a low pass filter (LPF) 32 smoothing an output signal of D/A converter 31, an amplifier 33 amplifying an output signal of low pass filter 32, and speaker 4 generating a sound wave according to an output signal of amplifier 33.

Error detecting portion 40 includes error detecting microphone 2, an amplifier 41 amplifying an output signal of microphone 2, a low pass filter (LPF) 42 passing a predetermined low frequency component of an output signal of amplifier 41, and an analog/digital (A/D) converter 43 converting an output signal of low pass filter 42 into a digital signal.

The input/output relation in a path of sound wave generating portion 30 and error detecting portion 40 is represented by a transfer function H(z). Although the transfer function H(z) is determined depending on where the controller is installed, a filter implementing the estimated transfer function H'(z) is provided in adapting portion 50, as will be described later. Adapting portion 50 adjusts the filter coefficients of signal processing portion 20 according to the estimated transfer function H'(z).

FIG. 3 is a diagram showing a configuration of signal processing portion 20 and adapting portion 50 shown in FIG. 2. Referring to FIG. 3, signal processing portion 20 includes an all zero filter 21 performing a moving average processing of input signal x(n) to provide a signal u(n), and an all pole filter 22 generating present output signal y(n) from signal u(n) and past feedback signals of output signal y(n).

All zero filter 21 includes cascade-connected N delay elements ($Z^{-1}$) 21*a*, (N+1) multipliers 21*b* provided corresponding to delay elements 21*a* for multiplying an output signal x(n−i) of corresponding delay element 21*a* and a coefficient $a_i$, and N adders 21*c* provided corresponding to multipliers 21*b*. Delay element 21*a* delays an applied signal by one cycle (sampling period). Multiplier 21*b* at the first stage multiplies input signal x(n) and a coefficient $a_0$. Adder 21*c* adds an output signal of an adder at the preceding stage and an output signal of a corresponding multiplier. All zero filter 21 carries out the following processing:

$$u(n) = \sum_{i=0}^{N} a_i(n) \cdot x(n-i) \tag{1a}$$

where $a_i(n)$ represents the value of coefficient $a_i$ at time n, and x(n−i) represents an output of delay element 21*a* at the i-th stage.

All pole filter 22 includes cascade-connected M-stages of delay elements 22*a* receiving output signal y(n), M multipliers 22*b* provided corresponding to delay elements 22*a*, and cascade-connected M adders 22*c* provided corresponding to multipliers 22*b*. Multiplier 22*b* multiplies an output signal y(n−j) of a corresponding delay element 22*a* and a coefficient $b_j(n)$. Adder 22*c* adds an output signal of corresponding multiplier 22*b* and an output signal of the adder 22*c* at the preceding stage. Adder 22*c* at the final stage adds output signal u(n) of all zero filter 21 and an output signal of the adder 22*c* at the preceding stage in the cascade connection. By using a configuration in which output signal y(n) is fed back, it is intended to increase the speed of convergence and to decrease the size of the controller. All pole filter 22 carries out the following processing:

$$y(n) = u(n) + \sum_{j=1}^{M} b_j(n) \cdot y(n-j) \tag{1b}$$

All zero filter 21 and all pole filter 22 are cascade-connected to form a direct form IIR (Infinite Impulse Response) digital filter. The following expression (1*c*) is obtained based on the expressions (1*a*) and (1*b*):

$$y(n) = \sum_{i=0}^{N} a_i(n) \cdot x(n-i) + \sum_{j=1}^{M} b_j(n) \cdot y(n-j) \tag{1c}$$

Adapting portion 50 updates coefficients $a_i$ and $b_j$. Adapting portion 50 includes a filter 51 transferring input signal x(n) according to the estimated transfer function H'(z), a coefficient update operating portion 52 updating coefficient $a_i$ of all zero filter 21 according to error signal e(n) and an output signal of filter 51, a filter 53 transferring output signal y(n) according to the estimated transfer function H'(z), and a coefficient update operating portion 54 updating coefficient $b_j$ of all pole filter 22 according to an output signal of filter 53 and error signal e(n). As to the estimated transfer function H'(z) of filters 51 and 53, the configuration and operation thereof will be described later. The estimated transfer function H'(z) of filters 51 and 53 is set in advance upon modeling for practical use. The output signals of filters 51 and 53 are represented by the following expressions (2*a*), (2*b*), respectively:

$$\sum_{k=0}^{L} h'_k \cdot x(n-k) \tag{2a}$$

$$\sum_{k=0}^{L} h'_k \cdot y(n-k) \tag{2b}$$

where $h'_k$ is a coefficient of z transformation of the estimated transfer function H'(z), and L represents the number of delay elements included in each of filters 51 and 53. Filters 51 and 53 carry out a filtering processing with applied signals over a time period (L+1).

Error signal e(n) is represented by the following expression (3):

$$\begin{aligned} e(n) &= d(n) + \sum_{k=0}^{L} h_k \cdot y(n-k) \\ &= d(n) + \sum_{k=0}^{L} h_k \cdot \left\{ \sum_{i=0}^{N} a_i(n-k) \cdot x(n-k-i) + \sum_{j=1}^{M} b_j(n-k) \cdot y(n-k-j) \right\} \\ &\cong d(n) + \sum_{i=0}^{N} a_i(n) \cdot \gamma_a(n-i) + \sum_{j=1}^{M} b_j(n) \cdot \gamma_b(n-j) \end{aligned} \tag{3}$$

where d(n) represents a desired response value described later, and $h_k$ represents a coefficient of z transformation of the transfer function H(z). $\gamma_a$, $\gamma_b$ are given by the following expressions (4*a*), (4*b*), respectively:

$$\gamma_a(n) = \sum_{k=0}^{L} h_k \cdot x(n-k) \tag{4a}$$

$$\gamma_b(n) = \sum_{k=0}^{L} h_k \cdot y(n-k) \tag{4b}$$

Upon derivation of the expression (3), the following expressions are assumed:

$$a_i(n-k) \simeq a_i(n)$$

$$b_j(n-k) \simeq b_j(n)$$

This assumption is equivalent to assumption that change of the coefficients $a_i(n)$, $b_j(n)$ during a time period L is sufficiently small.

With a square $e^2(n)$ of error signal e(n) an estimation function J, adapting portion 50 minimizes the estimation function J with a steepest descent method.

Update of the filter coefficients $a_i(n)$, $b_j(n)$ using the gradient method is given by the following expressions (5), (6):

$$a_i(n+1) = a_i(n) - 2 \cdot \mu \cdot e(n) \cdot \frac{\partial e(n)}{\partial a_i(n)} \tag{5}$$

$$b_j(n+1) = b_j(n) - 2 \cdot \nu \cdot e(n) \cdot \frac{\partial e(n)}{\partial b_j(n)} \tag{6}$$

where $\mu$, $\nu$ are step size parameters showing a unit amount upon update, which have small positive values.

Partial differentiation of the expression (3) by the filter coefficient $a_i(n)$ gives the following expression:

$$\begin{aligned} \frac{\partial e(n)}{\partial a_i(n)} &= \gamma_a(n-i) + \sum_{k=1}^{M} b_k(n) \frac{\partial \gamma_b(n-k)}{\partial a_i(n)}, \\ &\cong \gamma_a(n-i) + \sum_{k=1}^{M} b_k(n) \cdot \frac{\partial e(n-k)}{\partial a_i(n)} \end{aligned} \tag{7}$$

With $$\alpha_i(n) = \frac{\partial e(n)}{\partial a_i(n)}, \tag{8}$$

$$\alpha_i(n) = \gamma_a(n-i) + \sum_{k=1}^{M} b_k(n) \cdot \alpha_i(n-k)$$

Similarly, $$\beta_j(n) = \gamma_b(n-j) + \sum_{k=1}^{M} b_k(n) \cdot \beta_j(n-k) \tag{9}$$

where $$\beta_j(n) = \frac{\partial e(n)}{\partial b_j(n)},$$

$$\frac{\partial \gamma_b(n-k)}{\partial b_j(n)} \cong \beta_j(n-k).$$

With gradients $\alpha_i(n)$, $\beta_j(n)$ for the filter coefficients $a_i(n)$, $b_j(n)$ of the estimation function J (=$e^2(n)$), the expressions (5), (6) can be rewritten into the following expressions (10), (11):

$$a_i(n+1) = a_i(n) - 2\mu \cdot e(n) \cdot \alpha_i(n) \tag{10}$$

$$b_j(n+1) = b_j(n) - 2\nu \cdot e(n) \cdot \beta_j(n) \tag{11}$$

For simplicity of the updating operation shown by the expressions (10, (11), the following approximate expressions (12), (13) are used:

$$\alpha_i(n) \simeq \gamma_a(n-i) \tag{12}$$

$$\beta_j(n) \simeq \gamma_b(n-j) \tag{13}$$

The expressions (12), (13) can be obtained by ignoring the second term on the right side in the expressions (8), (9). With the expressions (12), and (13), the updating operation of the filter coefficients is given by the following expressions:

$$a_i(n+1) = a_i(n) - 2\mu \cdot e(n) \cdot \gamma_a(n-i) \tag{14}$$

$$b_j(n+1) = b_j(n) - 2\nu \cdot e(n) \cdot \gamma_b(n-j) \tag{15}$$

Filter 51 outputs the value $\gamma_a(n-i)$ in the expression (14), and filter 53 outputs the value $\gamma_b(n-j)$ in the expression (15). Coefficient update operating portion 52 updates the filter coefficients $a_0$–$a_N$ of all zero filter 21 according to the expression (14). Coefficient update operating portion 54 updates the filter coefficients of all pole filter 22 according to the expression (15).

The estimated transfer function H'(z) of filters 51 and 53 is often estimated according to an MA (Moving Average) model using a transversal filter. However, in order to reduce the order of a model (the number of stages of delay elements), there is also a case where it is estimated according to an ARMA (Auto-Regressive and Moving Average) model.

FIG. 4 is a diagram showing a configuration of filters 51 and 53 estimating the transfer function H(z) according to a conventional ARMA model. FIG. 4 shows a configuration of one filter.

Referring to FIG. 4, filter 51 (53) includes an identification object system 105 serving as a model for practical application, an all zero (MA) filter 121 receiving input signal x(n) to carry out filtering processing thereof, an all pole (AR) filter 122 filtering an output signal u(n) of all zero filter 121 to generate an output signal y(n), an adder 107 generating error signal e(n) (=d(n)−y(n)) from an output signal d(n) of identification object system 105 and output signal y(n) of all pole filter 122, a coefficient update operating portion 152 adjusting the filter coefficients of all zero filter 121 according to input signal x(n) and error signal e(n), and a coefficient update operating portion 153 adjusting the filter coefficients of all pole filter 122 according to error signal e(n) and output signal y(n).

As the input signal x(n), a white noise is applied upon identification of the system 105. After completion of identification of the system, the input signal x(n) shown in FIG. 3 is applied. In this case, or in practical use after the identification, the output y(n) of filter 122 becomes $\gamma_a(n)$ or $\gamma_b(n)$. Thus, in practical use, the error signal e(n) in the expression (3) includes the desired response value d(n).

Filters 121 and 122 each have a configuration similar to that of filters 21 and 22 shown in FIG. 3.

Identification object system 105 includes a sound wave generating portion 104 converting input signal x(n) into a sound signal, and a noise detecting portion 102 detecting the sound signal from sound wave generating portion 104. Identification object system 105 has a transfer function H(z). Filters 121 and 122 have their filter coefficients adjusted by coefficient update operating portions 152 and 153 such that the transfer function H(z) will be implemented.

In the configuration shown in FIG. 4, all zero filter 121 and all pole filter 122 are concatenated to form a direct form IIR digital filter. By the adaptive operation using error signal e(n), the transfer function H(z) is estimated. This configuration is the same as that shown in FIG. 3. With filter coefficients of filters 121 and 122 being $a_i(n)$ and $b_j(n)$, the coefficient updating operation is expressed by the following expressions:

$$e(n)=d(n)-y(n) \tag{16}$$

$$a_i(n+1)=a_i(n)+2\mu\cdot e(n)\cdot\alpha_i(n) \tag{17}$$

$$b_j(n+1)=b_j(n)+2\nu\cdot e(n)\cdot\beta_j(n) \tag{18}$$

In the expressions (17), (18), the same definition is used as the definition used upon derivation of the expressions (8) and (9). The following expressions can be obtained by making the approximation similar to that for the expressions (12), (13) for gradients $\alpha_i(n)$, $\beta_j(n)$:

$$\alpha_i(n)\simeq x(n-i) \tag{19}$$

$$\beta_j(n)\simeq y(n-j) \tag{20}$$

Therefore, the expressions (17), (18) can be rewritten into the following expressions:

$$a_i(n+1)=a_i(n)+2\mu\cdot e(n)\cdot x(n-i) \tag{21}$$

$$b_j(n+1)=b_j(n)+2\nu\cdot e(n)\cdot y(n-j) \tag{22}$$

According to the expressions (21) and (22), operating portions 152, 153 update the filter coefficients $a_i$, $b_j$ of filters 121, 122. With the post-adapted filter coefficients $a_i$, $b_j$, the estimated transfer function H'(Z) of the transfer function H(z) is represented by the following expression:

$$H'(z)=\frac{\sum_{i=0}^{N} a_i z^{-i}}{1-\sum_{j=1}^{M} b_j z^{-j}} \tag{23}$$

The estimated transfer function H'(z) has the filter coefficients $a_i$, $b_j$ set fixedly when the controller is actually operated to cancel an acoustic wave of noise or the like. It is needless to say that identification object system 105 is isolated, and not used.

In the algorithm represented by the expressions (14), (15), (21) and (22) used in the above-described filter coefficient updating operation, it is assumed that change of the filter coefficients $a_i(n)$, $b_j(n)$ over the time period L is small. However, stability of the filter is not guaranteed. More specifically, it is not taken into consideration where poles of all pole filters 22 and 122, which are recursive filters, are placed. It is required for stability of a recursive filter in general to place all the poles in a unit circle. In other words, when a convergence domain of a filter (a set of values of Z at which H(Z) exists) includes a unit circle, the filter is stable. The positions of the poles change according to values of the coefficients $b_j(n)$. Therefore, when the filter coefficients $b_j$ are updated, all pole filters 22, 122 sometimes become unstable to cause output signal y(n) not to converge but to diverge, leading to control decay.

When feedback from speaker 4 to microphone 2 is large in the configuration of FIG. 2 (when the gain is high), a resultant filter coefficient of a large value is generated by a large absolute value of the transfer function H(z). Therefore, in the actual active noise control operation, the optimum values of the filter coefficients $a_i$, $b_j$ approach an unstable domain (domain of non-convergence) of the filter per se. Therefore, by faulty adjustment of the filter coefficients caused by a spurious component such as disturbance, the filter is more likely to operate in the unstable domain. The stability of the IIR digital filter (all pole filter) is more likely to be influenced seriously.

In order to guarantee the stability of the filter, an SHARF (Simplified Hyperstable Adaptive Recursive Filtering) algorithm based on the concept of hyperstability is now proposed. In the SHARF algorithm, a signal v(n) defined by the following expression (24) is used instead of error signal e(n):

$$v(n)=e(n)+\sum_{i=1}^{P} w_i\cdot e(n-i) \tag{24}$$

The coefficient $w_i$ and the number P of used past error signals e(n) must be determined such that they satisfy a predetermined condition. However, since it is extremely difficult to actually determine these parameters $w_i$ and P, they are not suitable for practical use.

SUMMARY OF THE INVENTION

One object of the present invention is to provide an active controller which can carry out control operation stably with a simple configuration.

Another object of the present invention is to provide an active controller using an IIR digital filter in which the stability of the IIR digital filter is not damaged upon adaptive updating operation of a filter coefficient.

Still another object of the present invention is to provide a system identification apparatus for an active controller, which can carry out system identification reliably.

A further object of the present invention is to provide an active acoustic wave attenuation apparatus operating stably.

The active controller according to the present invention uses a lattice-type all pole filter concatenated to an all zero filter as an IIR digital filter.

Since it is possible to place all the poles of the lattice-type all pole filter in a unit circle by setting the absolute value of the filter coefficient less than one, the stability of the filter can be easily guaranteed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
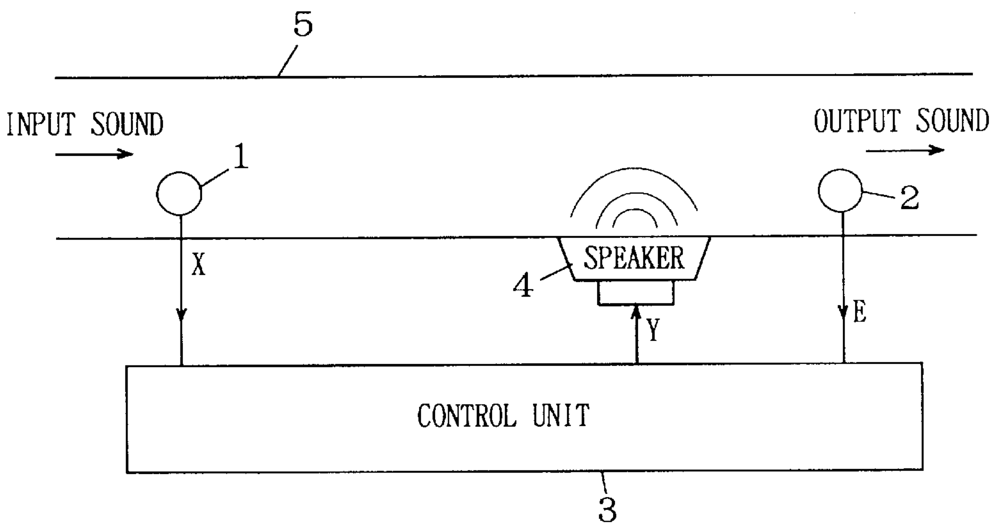
FIG. 1 PRIOR ART
FIG. 1 schematically shows the entire configuration of a conventional active noise controller.
Figure 2:
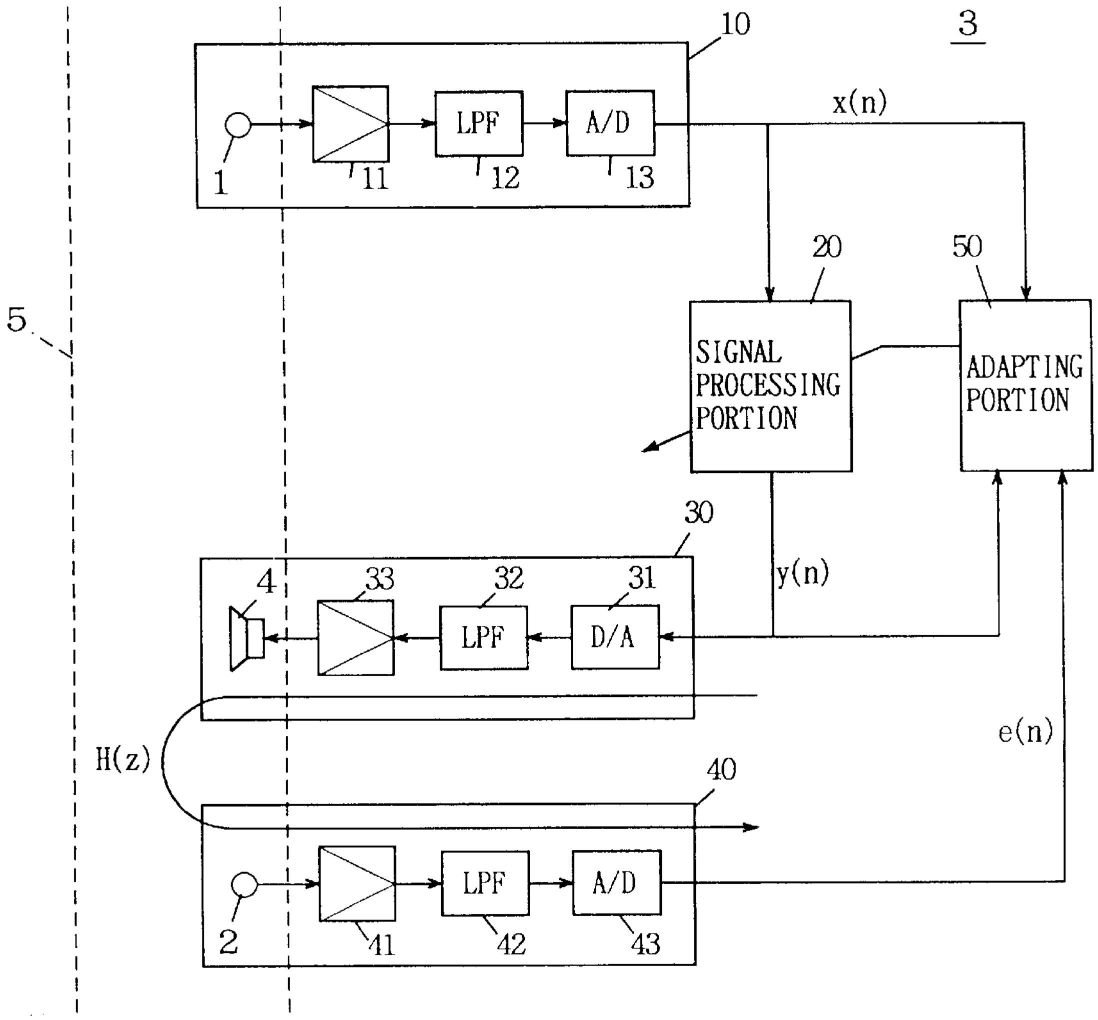
FIG. 2 PRIOR ART
FIG. 2 shows a configuration of a control unit shown in FIG. 1.
Figure 5:
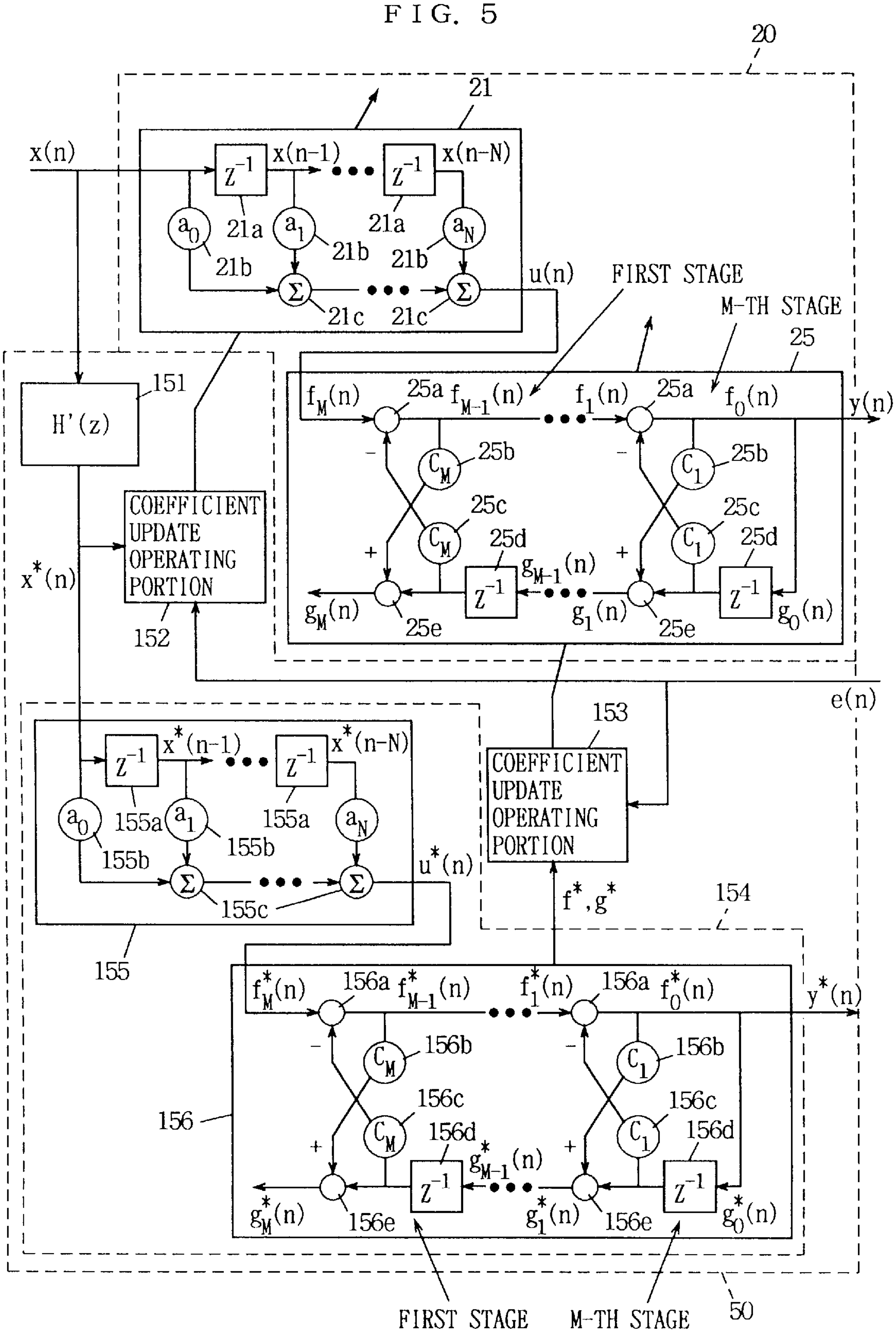
FIG. 5 shows a configuration of a main portion of an active controller according to an embodiment of the present invention.

FIG. 5 shows a configuration of a main portion of an active noise controller according to an embodiment of the present invention. In FIG. 5, the configuration of a signal processing portion and an adapting portion is shown. The configuration of a noise detecting portion, a sound wave generating portion, and an error signal detecting portion is the same as that of the conventional active noise controller shown in FIG. 2.

Referring to FIG. 5, signal processing portion 20 includes all zero filter 21 receiving noise signal (input signal) x(n) provided from noise detecting portion 10, filtering the received signal, and providing signal u(n), and a lattice-type all pole filter 25 filtering the output signal u(n) of all zero filter 21 to provide the signal y(n). Signal y(n) is applied to sound wave generating portion 30 shown in FIG. 2.

All zero filter 21 includes cascaded N-stages of delay elements 21*a*, (N+1) multipliers 21*b* provided corresponding to input signal x(n) and delay elements 21*a*, and N-staged adders 21*c* provided corresponding to multipliers 21*b*. Delay element 21*a* delays an applied signal by one cycle. Multiplier 21*b* multiplies output signal x(n−i) of corresponding delay element 21*a* and a filter coefficient $a_i$. Multiplier 21*b* at the first stage multiplies the input signal x(n) and a filter coefficient $a_0$. Adder 21*c* adds an output signal $a_i \cdot x(n-i)$ of corresponding multiplier 21*b* and an output signal of adder 21*c* at the preceding stage in the cascade connection. Adder 21*c* at the first stage adds an output signal $a_0 \cdot x(n)$ of multiplier 21*b* at the first stage and an output signal $a_1 \cdot x(n-1)$ of a corresponding multiplier 21*b*. All zero filter 21 has a configuration of a non-recursive filter. All zero filter 21 generates signal u(n) shown by the following expression (25) at time n similar to the all zero filter shown in FIG. 3:

$$u(n) = \sum_{i=0}^{N} a_i(n) \cdot x(n-i) \tag{25}$$

Lattice-type digital filter 25 includes M-staged adders 25*a* generating a forward signal f from output signal u(n) of all zero filter 21, multipliers 25*b* provided corresponding to adders 25*a*, cascade-connected (M)-staged delay elements 25*d* generating a backward signal g from the output signal y(n) (=$f_0$(n)) of filter 25, multipliers 25*c* provided corresponding to delay elements 25*e*, and adders 25*d* arranged alternately with delay elements 25*d*.

Lattice-type all pole filter 25 includes M-staged units, wherein one unit stage is formed of adders 25*a* and 25*e*, multipliers 25*b* and 25*c*, and delay element 25*d*. In each unit, multiplier 25*b* multiplies an output signal $f_m$(n) of adder 25*a* and a filter coefficient $C_m$, and applies the multiplication result to one input of adder 25*e*. Multiplier 25*c* multiplies an output signal $g_{m-1}$(n−1) of delay element 25*d* and the filter coefficient $C_m$, and applies the multiplication result to a negative input of adder 25*a*. Adder 25*a* subtracts an output signal of multiplier 25*c* from an output signal $f_m$(n) of adder 25*a* at the preceding stage. Adder 25*e* adds an output signal of multiplier 25*b* and an output signal of delay element 25*d*. Therefore, forward output $f_{m-1}$(n) and backward output $g_m$(n) for forward input $f_m$(n) and backward input $g_{m-1}$(n) of the m−th stage at time n are given by the following expressions:

$$f_{m-1}(n)=f_m(n)-C_m(n)\cdot g_{m-1}(n-1) \tag{26}$$

$$g_m(n)=g_{m-1}(n-1)+C_m(n)\cdot f_{m-1}(n) \tag{27}$$

for m=1, 2, . . . M.

$$f_M(n)=u(n) \tag{28}$$

$$f_0(n)=g_0(n)=y(n) \tag{29}$$

From the expression (26)

$$\sum_{m=1}^{M}(f_{m-1}(n))-f_m(n)=f_0-f_M$$

Therefore, $$f_0-f_M=y(n)-u(n)=-\sum_{m=1}^{M}C_m(n)\cdot g_{m-1}(n-1), \tag{30}$$

That is, $$\begin{aligned} y(n) &= u(n)-\sum_{m=1}^{M}c_m(n)\cdot g_{m-1}(n-1) \\ &= \sum_{i=0}^{N}a_i(n)\cdot x(n-i)-\sum_{m=1}^{M}C_m(n)\cdot g_{m-1}(n-1) \end{aligned} \tag{31}$$

As is clear from the expression (30), lattice-type all pole filter 25 feeds back the output signal y(n), and generates a new output signal y. Lattice-type all pole filter 25 is equivalent to recursive filter 22 shown in FIG. 3. Therefore, as is clear from the expression (31), signal processing portion 20 is equivalent to a direct form IIR digital filter.

In lattice-type all pole filter 25, if the absolute value of the filter coefficient $C_m$ is less than one, absolute values of positions of all the poles become smaller than one, and all the poles are placed in a unit circle. Therefore, lattice-type all pole filter 25 operates stably without causing divergence, converging output signal y(n). In other words, the stability of filter 25 is guaranteed. The limitation of the filter coefficient $C_m(n)$ of lattice-type all pole filter 25 is carried out by the coefficient update operating portion 153 described later.

Adapting portion 50 includes reference filter 151 having the transfer function H'(z) and receiving input signal x(n) to generate a reference signal x*(n), and coefficient update operating portion 152 adjusting the filter coefficient $a_i(n)$ of all zero filter 21 according to reference signal x*(n) from reference filter 151 and error signal e(n) from the error detecting portion.

Similar to all zero filter 21, reference filter 151 has a configuration of a transversal filter, and carries out the following filtering processing:

$$x^*(n)=\sum_{R=0}^{L}h_k\cdot x(n-k) \tag{32}$$

where $h_k$ is a filter coefficient implementing the transfer function H'(z) of filter 151 which is predetermined upon system identification. L is the number of stages of delay elements of reference filter 151 which is appropriately determined. L may be equal to N.

Adapting portion 50 further includes a reference filter 154 filtering the reference signal x*(n) from reference filter 151 to generate a reference signal y*(n), and coefficient update operating portion 153 adjusting the filter coefficient $C_m(n)$ of lattice-type all pole filter 25 according to reference signal y*(n) provided from reference filter 154 and error detect signal e(n) from the error detecting portion.

Reference filter 154 has the same configuration as signal processing portion 20 and includes an all zero filter 155 in a transversal filter form filtering reference signal x*(n) from reference filter 151 to generate a signal u*(n), and a lattice-type all pole filter 156 filtering output signal u*(n) of all zero filter 155 to generate signal y*(n).

All zero filter 155 includes n-staged cascaded delay elements 155*a* having the same configuration as all zero filter 21 of signal processing portion 20, multipliers 155*b* provided corresponding to input signal x*(n) and delay elements 155*a*, and cascaded n-staged adders 155*c* provided corresponding to multipliers 155*b*.

Multiplier 155*b* has a filter coefficient $a_{i(n)}$. The value of the filter coefficient $a_i(n)$ of the transversal filter 21 included in signal processing portion 20 is copied into the coefficient $a_i(n)$ of the multiplier 155*b*. The filter coefficient $a_i(n)$ of the sampling. Thus, the initial value of the coefficient may be zero. Signal u*(n) indicated by the following expression is provided from all zero filter 155:

$$u^*(n)=\sum_{i=0}^{N}a_i(n)\cdot x^*(n-i) \tag{33}$$

Lattice-type all pole filter 156 has the same configuration as lattice-type all pole filter 25, and includes cascaded adders (subtractors) 156*a*, multipliers 156*b* provided at output portions of adders 156*a*, delay elements 156*d* each delaying an applied signal by one cycle, adders 156*e* arranged alternately with delay elements 156*d*, and multipliers 156*c* provided at output portions of delay elements 156*d*.

Adders 156*a*, 156*e*, multipliers 156*b*, 156*c*, and delay element 156*d* form a unit stage. In each unit stage, adder 156*a* receives an output signal of adder 156*a* at the preceding stage at a positive input, and receives an output signal of multiplier 156*c* at a negative input. Adder 156*e* adds an output signal of multiplier 156*b* and an output signal of delay element 156*d*. Multipliers 156*b* and 156*c* have the same filter coefficients. Now, represent the forward input and the backward input at the m-th stage at time n by $f_m^*(n)$ and $g_{m-1}^*(n)$, respectively, with $y^*(n)=f_0^*(n)$.

Reference filter 154 carries out the same processing as the IIR filter of signal processing portion 20. Referring to the expressions (26) to (31), the following expression is found:

$$y^*(n)=\sum_{i=0}^{N}a_i(n)\cdot x^*(n-i)-\sum_{m=1}^{M}C_m(n)\cdot g^*_{m-1}(n-1) \tag{34}$$

As for the filter coefficient $C_m(n)$ of lattice type filter 156, the value of the filter coefficient $C_m(n)$ of lattice type filter 25 sampling, similar to that of multiplier 155*b*.

Assume that change of the filter coefficients $a_i(n)$, $C_m(n)$ of filters 21 and 25 during time period L is sufficiently small. Error signal e(n) is represented by the following expression using reference signal y*(n):

$$\begin{aligned} e(n) &\cong d(n)+y^*(n) \\ &= d(n)+\sum_{i=0}^{N}a_i(n)\cdot x^*(n-i)-\sum_{m=1}^{M}C_m(n)\cdot g^*_{m-1}(n-1) \end{aligned} \tag{35}$$

where d(n) indicates a desired response value.

Assume that square error $e^2(n)$ is estimation function J. The estimation function J is minimized according to a gradient method. In this case, the filter coefficients $a_i(n)$ and $C_m(n)$ of all zero filter 21 and lattice-type all pole filter 25 are updated according to the following expressions:

$$a_i(n+1)=a_i(n)-2\cdot\mu\cdot e(n)\frac{\partial y^*(n)}{\partial a_i(n)} \tag{36}$$

$$C_m(n+1)=C_m(n)-2\cdot\nu\cdot e(n)\frac{\partial y^*(n)}{\partial C_m(n)} \tag{37}$$

where $\mu$, ν are step size parameters having small positive values showing update unit amount.

From the expression (35), the following expression is obtained:

$$\frac{\partial y^*(n)}{\partial a_i(n)} = x^*(n-i) - \sum_{j=1}^{M} C_j(n) \cdot \frac{\partial g^*_{j-1}(n-1)}{\partial a_i(n)} = x^*(n-i) - \sum_{j=1}^{M} C_j(n) \cdot \frac{\partial g^*_{j-1}(n-1)}{\partial a_i(n-1)} \quad (38)$$

Similarly, $$\frac{\partial y^*(n)}{\partial C_m(n)} = -g^*_{m-1}(n-i) - \sum_{j=1}^{M} C_j(n) \cdot \frac{\partial g^*_{j-1}(n-1)}{\partial C_m(n-1)} \quad (39)$$

In the expressions (38) and (39), the following approximate expressions are used:

$$\frac{\partial g^*_{j-1}(n-1)}{\partial a_i(n)} \cong \frac{\partial g^*_{j-1}(n-1)}{\partial a_i(n-1)} \quad (40)$$

$$\frac{\partial g^*_{j-1}(n-1)}{\partial C_m(n)} \cong \frac{\partial g^*_{j-1}(n-1)}{\partial C_m(n-1)} \quad (41)$$

In order to simplify operation of the expressions (38) and (39), the following approximation algorithms are used:

$$\frac{\partial y^*(n)}{\partial a_i(n)} \cong x^*(n-i) \quad (42)$$

$$\frac{\partial y^*(n)}{\partial C_m(n)} \cong -g^*_{m-1}(n-1) \quad (43)$$

The fact that changes of the coefficients $a_i(n)$ and $C_m(n)$ are sufficiently small during a time period M, and that change of backward signal $g_m{}^*(n)$ is also small is used in the expressions (42), (43).

Finally, the update expressions of the filter coefficients $a_i(n)$ and $C_m(n)$ of all zero filter 21 and all pole filter 25 are given as follows:

$$a_i(n+1)=a_i(n)-2\cdot\mu\cdot e(n)\cdot x^*(n-i) \quad (44)$$

$$C_m(n+1)=C_m(n)+2\cdot\nu\cdot e(n)\cdot g^*_{m-1}(n-1) \quad (45)$$

More specifically, using signals x*(n−1) generated by filters 151 having the filter coefficients $h_k$ set upon system identification and the signal $g^*_{m-1}(n-1)$ generated by the filters 155 and 156 having the filter coefficients $a_1(m)$ and $C_m(n)$ copied from the filters 21 and 25 of the signal processing portion 20, the filter coefficients $a_i(n)$ and $C_m(n)$ of all zero filter 21 and all pole filter 25 are adaptively adjusted.

Coefficient update operating portion 152 updates the filter coefficient $a_i(n)$ of all zero filter 21 using reference signal x*(n−i) provided from reference filter 151 and error signal e(n) according to the expression (44).

Coefficient update operating portion 153 updates the filter coefficient $C_m(n)$ of lattice-type all pole filter 25 using error signal e(n) and backward signal $g_{m-1}{}^*(n-1)$ of filter 156 according to the expression (45).

Figure 6:
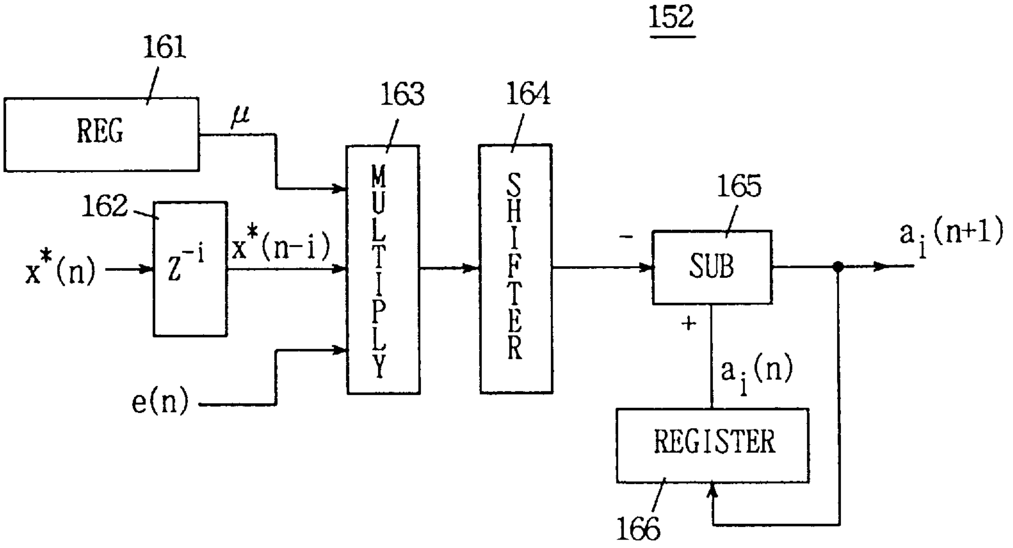
FIG. 6 shows a configuration of an update operating portion updating filter coefficients of an all zero filter shown in FIG. 5.

FIG. 6 is a diagram showing the configuration of coefficient update operating portion 152 shown in FIG. 5. Referring to FIG. 6, coefficient update operating portion 152 includes a register 161 storing a step size parameter $\mu$, a delay element 162 delaying reference signal x*(n) of reference filter 151 by i cycles, a multiplier 163 multiplying step size parameter $\mu$, reference signal x*(n−i) provided from delay element 162, and error signal e(n), a shifter (shift register) 164 shifting bit positions of an output signal (multi-bit digital signal) of multiplier 163 to implement doubling operation, a register 166 storing the filter coefficient $a^i(n)$, and a subtractor 165 subtracting an output signal of shifter 164 from the filter coefficient $a^i(n)$ provided from register 166.

The post-updated filter coefficient $a_i(n+1)$ is provided from subtractor 165. The filter coefficient $a_i(n)$ stored by register 166 is rewritten by the filter coefficient $a_i(n+1)$ after updated.

Delay element 162 may be common with delay element 155*a* included in filter 155. The configuration shown in FIG. 6 is provided for each filter coefficient $a_i$, and updated filter coefficient $a_i(n+1)$ is applied to corresponding multiplier 21*b*.

Figure 7:
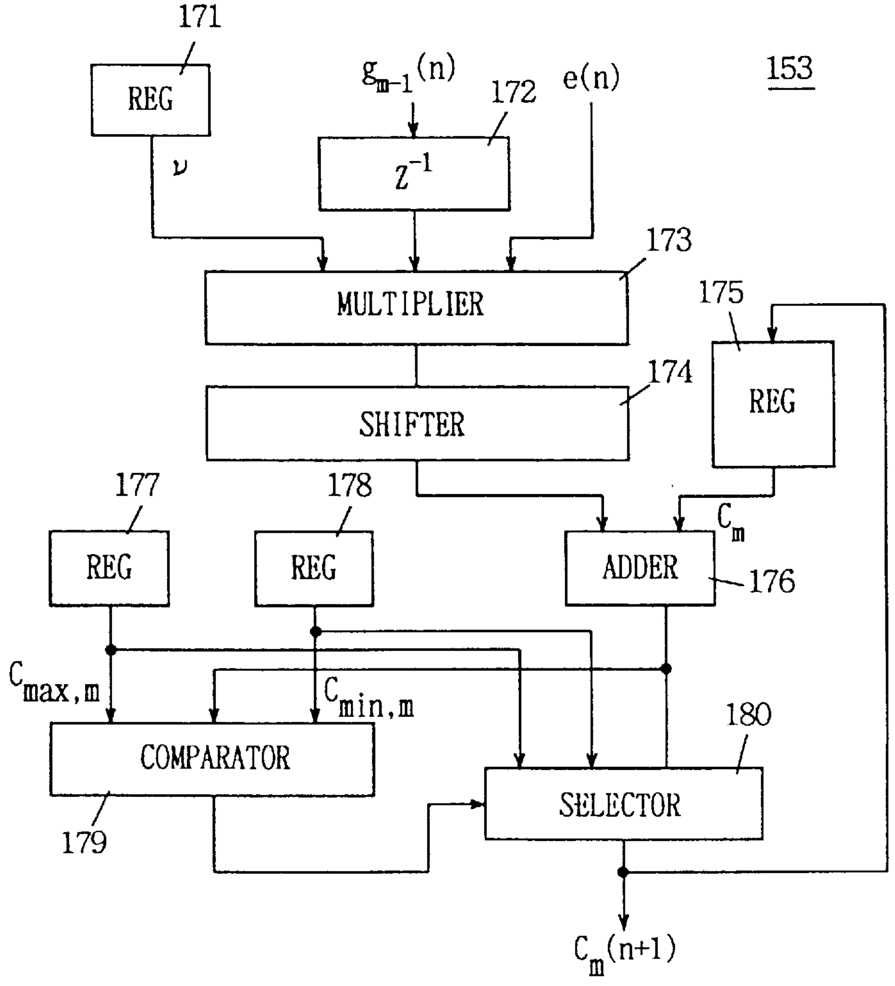
FIG. 7 shows a configuration of an update operating portion updating filter coefficients of an all pole filter shown in FIG. 5.

FIG. 7 is a diagram showing a configuration of coefficient update operating portion 153 shown in FIG. 5. Referring to FIG. 7, coefficient update operating portion 153 includes a register 171 storing a step size parameter ν, a delay element 172 delaying backward signal $g_{m-1}(n)$ of reference filter 156 by one cycle, a multiplier 173 multiplying parameter ν, output signal $g_{m-1}(n-1)$ of delay element 172 and error signal e(n), a shifter 174 shifting up an output signal (multi-bit digital signal) of multiplier 173 by one bit to implement doubling operation, a register 175 storing the filter coefficient $C_m(n)$, and an adder 176 adding an output signal of shifter 174 and an output signal of register 175. Shifter 174 may be configured of a shift register, or may be simply formed by interconnection lines only.

Operating portion 153 further includes registers 177 and 178 respectively storing the upper limit value $C_{max,\ m}$ and the lower limit value $C_{min,\ m}$ of the filter coefficient $C_m$, a comparator 179 comparing an output signal of adder 176 with the upper limit value $C_{max,\ m}$ and the lower limit value $C_{min,\ m}$ held by registers 177 and 178, and a selector 180 selectively passing one of the output signal of adder 176, the upper limit value $C_{max,\ m}$, and the lower limit value $C_{min,\ m}$, according to an output signal of comparator 179.

Respective absolute values of the upper limit value $C_{max,\ m}$ and the lower limit value $C_{min,\ m}$ set in registers 177 and 178 are made smaller than one. The upper limit value $C_{max,\ m}$ and the lower limit value $C_{min,\ m}$ may be set to each filter coefficient $C_m$, or upper and lower limit values common to all the filter coefficients $C_1$ to $C_M$ of all pole filter 25 may be set.

Comparator 179 provides a signal indicating that the value of the output signal of adder 176 is (i) the upper limit value $C_{max,\ m}$ or more, (ii) between the upper limit value $C_{max,\ m}$ and the lower limit value $m_{min,\ m}$, or (iii) the lower limit value $C_{min,\ m}$ or less. Such a configuration of comparator 179 is implemented by a comparing circuit comparing the lower limit value $C_{min,\ m}$ with the output signal of adder 176, and a comparing circuit comparing the output signal of adder 176 with the upper limit value $C_{max,\ m}$. Selector 180 selects the upper limit value $C_{max,\ m}$ from register 177 when comparator 179 indicates the above state (i). Selector 180 selects the output signal of adder 176 when comparator 179 indicates the above state (ii). Selector 180 selects the lower limit value $C_{min,\ m}$ from register 178 when comparator 179 indicates the above state (iii).

The updated filter coefficient $C_m(n+1)$ is provided from selector 180, and applied to corresponding multipliers 25*b* and 25*c* of lattice-type all pole filter 25. The updated filter coefficient $C_m(n+1)$ from selector 180 is applied to register 175, and stored therein.

By comparator 179 and selector 180, the filter coefficient $C_m(n)$ has its absolute value always set to a value smaller than one. Therefore, in adaptive operation, the stability of lattice-type all pole filter 25 in signal processing portion 20 is not damaged. More specifically, the stability of IIR digital filter formed of all zero filter 21 and all pole filter 25 is not damaged in adaptive control operation of the filter coefficients $a_i(n)$ and $C_m(n)$. Even if faulty adjustment is made due to disturbance or the like, the stability of lattice-type all pole filter 25 is always guaranteed because the filter coefficients are clipped. Accordingly, the stability of the IIR digital filter is guaranteed.

[Modification]

The second term of the expression (39) is approximated by the following expression taking the expressions (26), (27) into consideration:

$$A = \sum_{j=1}^{M} C_j(n)\cdot\frac{\partial g^*_{j-1}(n-1)}{\partial C_m(n-1)} = \sum_{j=1}^{M} C_j(n)\cdot \frac{\partial}{\partial C_m(n-1)}\{g^*_{j-2}(n-2)+C_{j-1}(n-1)\cdot f^*_{j-2}(n-1)\} \quad (46)$$

By ignoring the term of $\{\partial g^*_j(n-2)\}/(\partial C_m(n-2)\}$, and using the expressions $\psi_m(n)$ and $\phi_m(n)$ defined by the following expressions, the expression (46) is approximated as follows:

$$\psi_m(n) = 2f^*_{m-1}(n-1) - f^*_m(n-1);\ \text{for } m = 1\sim M \quad (47)$$

$$\phi_m(n) = C_{m+1}(n)\cdot C_m(n-1) + \phi_{m-1}(n);\ \text{for } m = 0\sim M-1 \quad (48)$$

$$A \cong C_{m+1}(n)\cdot\psi_m(n) - g^*_{m-1}(n-2)\cdot\phi_{m-1}(n) \quad (49)$$

where $\phi_{m-1}(n) = 0$ for $m = 0$.

The expression (48) is converted into the following expression (50):

$$\phi_m(n) - \phi_{m-1}(n) = C_{m+1}(n)\cdot C_m(n-1) \quad (50)$$

therefore $$\phi_m = \sum_{j=0}^{m} C_{j+1}(n)\cdot C_j(n-1)$$

where $C_0=1$

The filter coefficient $C_m(n)$ is updated according to the following expression:

$$\begin{aligned} C_m(n+1) &= C_m(n) - 2\cdot\nu\cdot e(n)\{-g^*_{m-1}(n-1) - A\} \quad (51)\\ &= C_m(n) + 2\cdot\nu\cdot e(n)g^*_{m-1}(n-1) + 2\cdot\nu\cdot e(n)\cdot \{C_{m+1}(n)\cdot\psi_m(n) - g^*_{m-1}(n-2)\cdot\phi_{m-1}(n)\}\end{aligned}$$

Although operation for the third term is increased, the amount of calculation is in the order of the order number M of lattice-type all pole filter 25. The operation time is not much increased, and real time processing can be implemented.

Also in the configuration of this modification, when the filter coefficient $C_m(n)$ exceeds the upper limit value or the lower limit value, the filter coefficient $C_m(n)$ is clipped to the exceeded limit value. Since precision of approximation is improved, the filter coefficient is updated adaptively with higher precision.

Although the configuration for updating the filter coefficient $C_m(n)$ according to the expression (51) is not shown particularly, the hardware configuration will be apparent from the expression (50). The hardware configuration will be described later.

Figure 8:
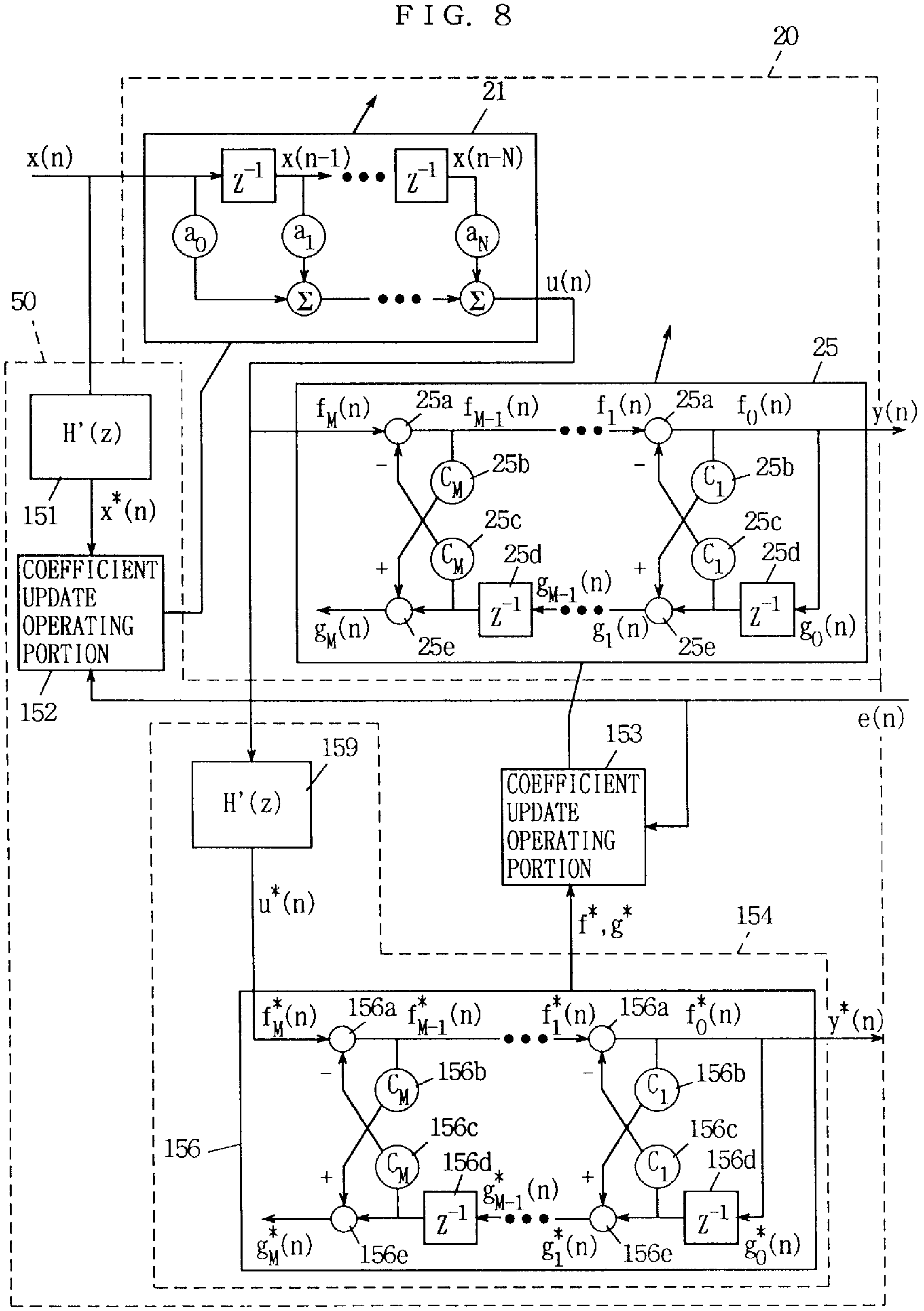
FIG. 8 shows a configuration of a main portion of an active controller according to another embodiment of the present invention.

FIG. 8 is a diagram showing a configuration of the second embodiment of signal processing portion 20 and adapting portion 50. In the configuration shown in FIG. 8, reference filter 154 for updating the filter coefficients of lattice-type all pole filter 25 includes a filter 159 filtering output signal u(n) of all zero filter 21 to generate reference output signal u*(n), and a filter 156 filtering output signal u*(n) of filter 159.

Filter 159 has the transfer function H'(z), having the same configuration as filter 151. Filter 156 has the same configuration as filter 156 shown in FIG. 5. The other configuration is the same as that shown in FIG. 5, and the same reference characters are applied to corresponding portions.

Filter 159 is formed of a transversal filter, and generates signal u*(n) represented by the following expression:

$$\begin{aligned} u^*(n) &= \sum_{K=0}^{L} h_k\cdot u(n-k) \quad (52)\\ &= \sum_{k=0}^{L} h_k\cdot\sum_{i=0}^{N} a_i(n)\cdot x(n-i-k)\\ &= \sum_{i=0}^{N} a_i(n)\cdot\sum_{k=0}^{L} h_k\cdot x(n-i-k)\\ &= \sum_{i=0}^{N} a_i(n)\cdot x^*(n-i)\end{aligned}$$

If change of the filter coefficient $a_i(n)$ of all zero filter 21 during time period L is sufficiently small, $x^*(n)\approx u(n)$, and the expression (52) is substantially equivalent to the expression (33). More specifically, the configuration shown in FIG. 8 can make an effect similar to the configuration shown in FIG. 5. Additionally, in the configuration shown in FIG. 8, update of the filter coefficient $a_i(n)$ of all zero filter 21 and update of the filter coefficient $C_m(n)$ of lattice-type all pole filter 25 can be implemented in separate paths.

Figure 9:
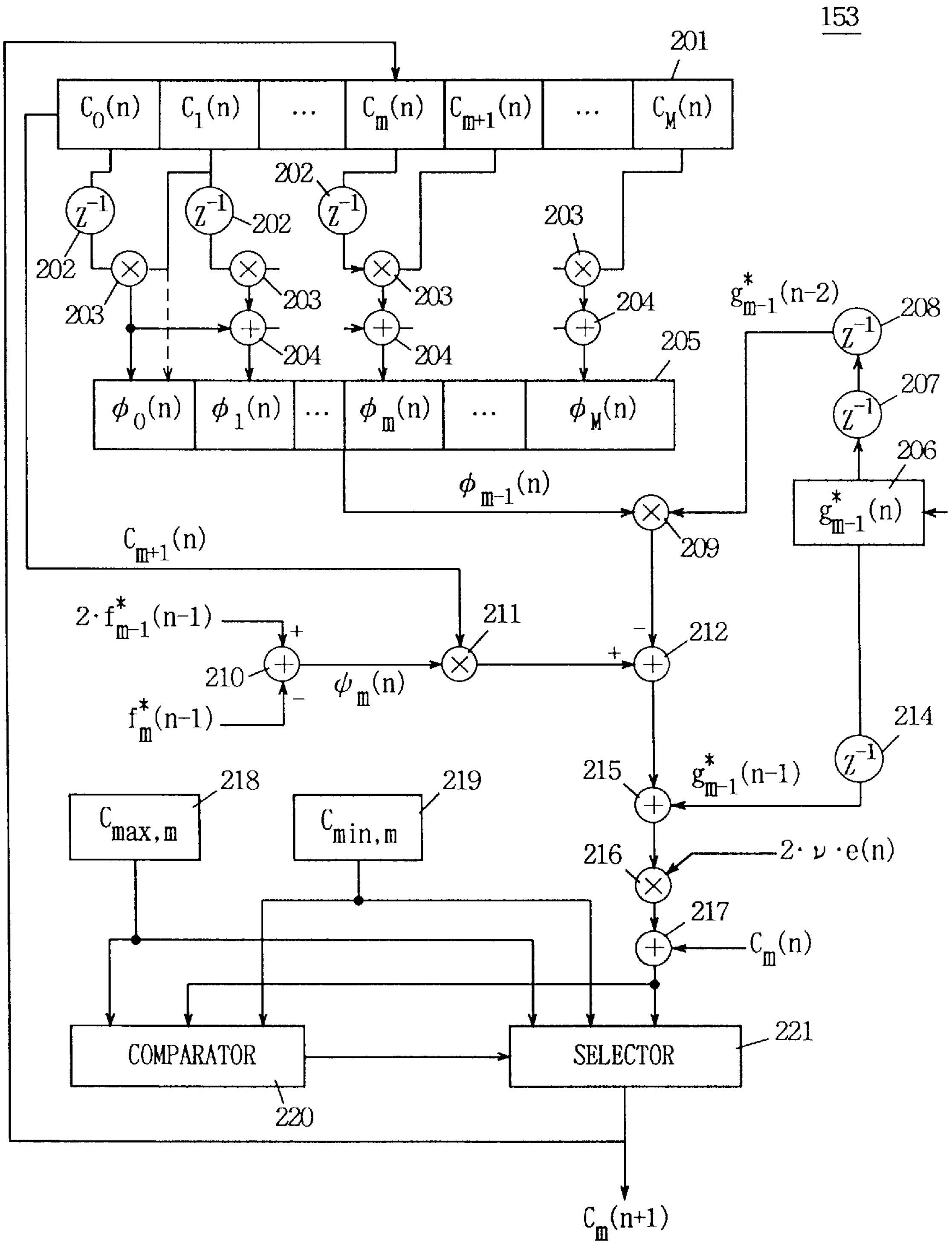
FIG. 9 shows another configuration of the update operating portion updating the filter coefficients of the all pole digital filter.

FIG. 9 is a diagram showing a configuration of coefficient update operating portion 153 updating the filter coefficient $C_m(n)$ according to the expression (51).

In FIG. 9, coefficient update operating portion 153 includes a register 201 storing filter coefficients $C_0(n)$–$C_M(n)$, delay elements 202 delaying the filter coefficients $C_0(n)$–$C_M(n)$ stored in register 201 by one cycle ($z^{-1}$), multipliers 203 multiplying output signal $C_j(n-1)$ of delay element 202 and a filter coefficient $C_{j+1}(n)$ from register 201, adders 204 each adding output signals of two adjacent multipliers 203, and a register 205 storing output signals of adders 204. Here, the coefficient $C_0$ is normally set to one. Therefore, as shown by a dotted arrow, the multiplier 203 and the delay circuit 202 at the leftmost position in FIG. 9 can be omitted.

Multiplier 203 outputs $C_j(n-1)\cdot C_{j+1}(n)$. Adder 204 generates $C_j(n-1)\cdot C_{j+1}(n)+\phi_{j-1}(n)=\phi_j(n)$. Operation of adder 204 will be apparent from $\phi_0(n)=C_1(n)\cdot C_0(n-1)$, $$\phi_1(n)=C_2(n)\cdot C_1(n-1)+\phi_0(n),\ \phi_2(n)=C_3(n)\cdot C_2(n-1)+\phi_1(n),$$

Operating portion 153 further includes a register 206 storing backward signal $g_{m-1}^*(n)$ from filter 156, delay elements 207 and 208 delaying data held by register 206 by two cycles in total and providing the delayed data, and a multiplier 209 multiplying output signal $g_{m-1}^*(n-2)$ of delay element 208 and signal $\phi_{m-1}(n)$ read out from register 205. $\phi_{m-1}(n)\cdot g_{m-1}^*(n-2)$ is provided from multiplier 209.

Operating portion 153 further includes a subtractor 210 subtracting delay signals of forward signals $2\cdot f_{m-1}^*(n)$ and $f_m^*(n)$ from filter 156, a multiplier 211 multiplying an output signal of subtractor 210 and the filter coefficient $C_{m+1}(n)$, and a subtractor 212 subtracting output signals of multipliers 209 and 211.

$2\cdot f_{m-1}(n-1)-f_m^*(n-1)$ is provided from subtractor 210. $C_{m+1}(n)\cdot\{2\cdot f_{m-1}^*(n-1)-f_m^*(n-1)\}=\psi_m(n)\cdot C_{m+1}(n)$ is provided from multiplier 211. $C_m(n)\cdot C_{m+1}(n)-\phi_{m-1}(n)\cdot g_{m-1}^*(n-2)$ is provided from subtractor 212. The output signal shown in the expression (49) is obtained from subtractor 212.

Operating portion 153 further includes a delay element 214 delaying data held by register 206 by one cycle to generate $g_{m-1}^*(n-1)$, an adder 215 adding an output signal of subtractor 212 and an output signal of delay element 214, a multiplier 216 multiplying an output signal of adder 215 and coefficient $2 \cdot \nu \cdot e(n)$, and an adder 217 adding an output signal of multiplier 216 and the filter coefficient $C_m(n)$ from register 201. The update coefficient shown in the expression (51) is provided from adder 217.

Operating portion 153 further includes registers 218 and 219 storing the upper limit value $C_{max, m}$ and the lower limit value $C_{min, m}$, a comparator 220 determining whether or not an output value of adder 217 is between the upper limit value and the lower limit value, and a selector 221 selecting any one of an output signal of adder 217, the upper limit value $C_{max, m}$ and the lower limit value $C_{min, m}$ according to an output signal of comparator 220.

The absolute values of the upper limit value $C_{max, m}$, and the lower limit value $C_{min, m}$, are made smaller than one. The configuration of comparator 220 and selector 221 is the same as shown in FIG. 7. When the output signal of adder 217 exceeds the upper limit value $C_{max, m}$, the upper limit value $C_{max, m}$ is selected, and when the output signal of adder 217 is smaller than the lower limit value $C_{min, m}$, the lower limit value $C_{min, m}$ is selected. When the output signal of adder 217 is between the upper limit value $C_{max, m}$ and the lower limit value $C_{min, m}$, the output signal of adder 217 is selected. An output signal of selector 221 is applied to a corresponding position of register 201 at which the filter coefficient is to be stored, and stored therein.

Even if approximation precision is improved as shown in FIG. 9, multiplication requiring a long operation time is only performed in two stages since multipliers 209, 211 operate in parallel. Therefore, it is possible to carry out filter coefficient update operation processing at a high speed.

Figure 10:
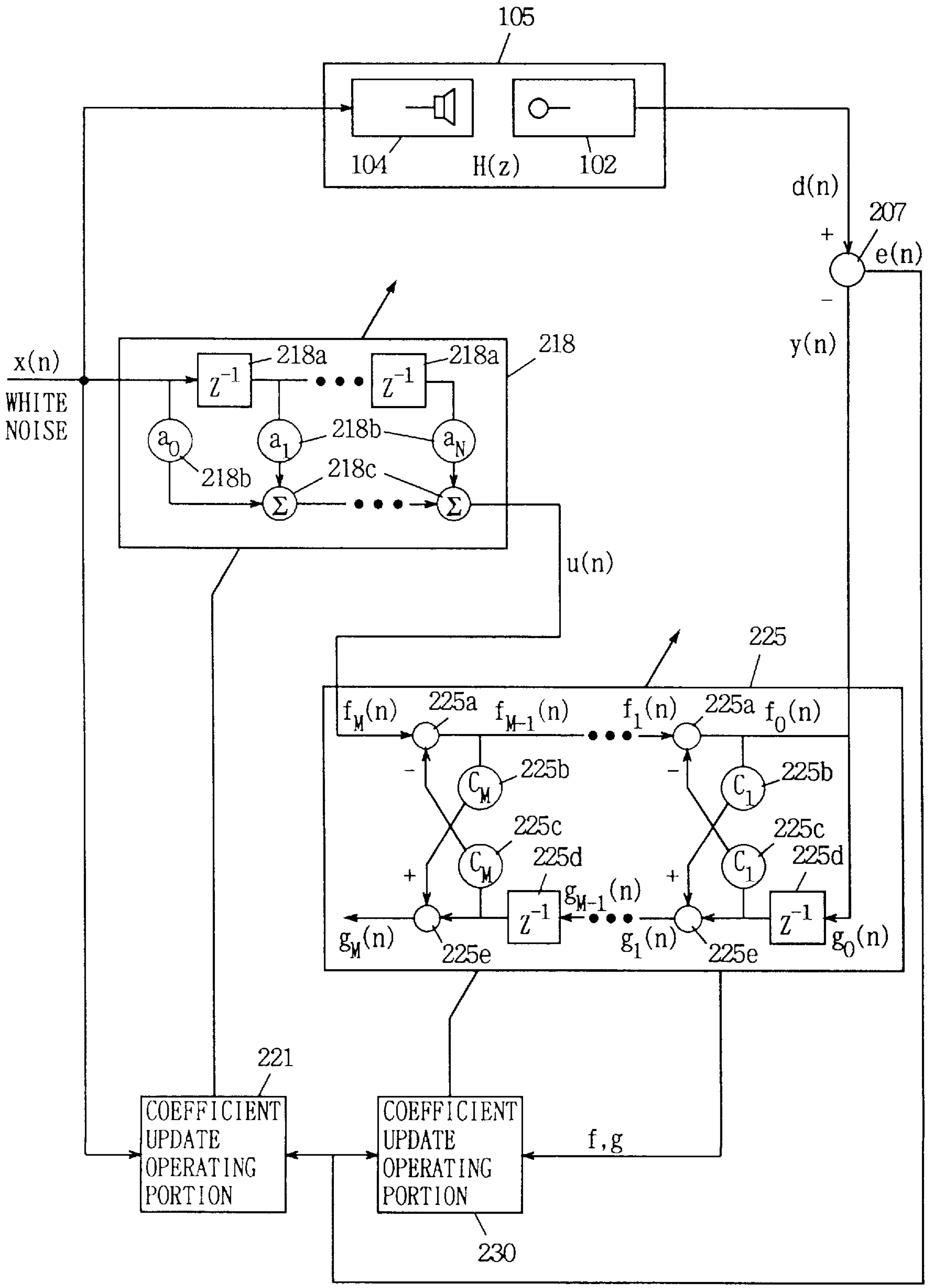
FIG. 10 shows a configuration of the system identification filter.

FIG. 10 is a diagram showing another configuration of the reference filter. As for reference filters 151 and shown in FIGS. 5 and 8, the transfer function H(z) is estimated according to the MA model. FIG. 10 shows the configuration for estimating the transfer function H(z) according to the ARMA model.

Referring to FIG. 10, identification object system 105 includes an error detecting portion 102 receiving an output signal of a sound wave generating portion 104 generating a sound wave corresponding to input signal x(n) formed of white noise (wideband noise) to generate a response signal d(n). Identification object system 105 has the transfer function H(z).

A system identification filter included in the adapting portion includes a transversal all zero filter 218 receiving input signal x(n), and a lattice-type all pole filter 225 cascaded to all zero filter 218.

All zero filter 218 includes cascaded N-stages of delay elements 218*a*, multipliers 218*b* having a filter coefficient $a_i$, and cascaded adders 218*c*. Signal u(n) represented by the following expression is provided from all zero filter 218 at time n:

$$u(n) = \sum_{i=0}^{N} a_i(n) \cdot x(n-i)$$

Lattice-type all pole filter 225 includes M-staged adders 225*a* receiving signal u(n), M-staged delay elements 225*d* receiving output signal $f_0(n)$ (=y(n)), M-staged adders 225*e* arranged alternately with delay elements 225*d*, multipliers 225*c* having a coefficient $C_m(n)$ provided corresponding to adders 225*a*, and multipliers 225*b* having the coefficient $C_m(n)$ provided corresponding to adders 225*e*.

If $f_m(n)$, $g_{m-1}(n)$, and $C_m(n)$ denote a forward input, a backward input and a filter coefficient, respectively, at the m-th stage at time n, forward output $f_{m-1}(n)$ and backward output $g_m(n)$ at the m-th stage are given by the following expressions:

$$f_{m-1}(n)=f_m(n)-C_m(n)\cdot g_{m-1}(n-1) \quad (53)$$

$$g_m(n)=g_{m-1}(n-1)+C_m(n)\cdot f_{m-1}(n) \quad (54)$$

These are the same as those of the lattice-type all pole filters shown in FIGS. 5 and 8. Error signal e(n) is represented by the following expression:

$$e(n)=d(n)-y(n) \quad (55)$$

Assuming that square error $e^2(n)$ is an estimation function J, the estimation function J is minimized according to the gradient method. The filter coefficients $a_i$, $C_m$ are estimated, and the transfer function H(z) is estimated accordingly. Based on the expressions (44) and (45), the filter coefficients $a_i$ and $C_m$ are updated according to the following expressions:

$$a_i(n+1)=a_i(n)+2\cdot\mu\cdot e(n)\cdot x(n-i) \quad (56)$$

$$C_m(n+1)=C_m(n)-2\cdot\nu\cdot e(n)\cdot g_{m-1}(n-1) \quad (57)$$

The sign of the second terms on the right sides of the expressions (56) and (57) is opposite to that of the expressions (44) and (45), because the sign of output signal y(n) in definition of error signal e(n) is different. Update of the filter coefficients is completed when an expected value of $e^2(n)$ attains predetermined value or less. Therefore, the above-described difference of sign does not have any significant meaning. The same definition of error signal may be used. Here, it should be noted that the signs of the second terms at the right sides of the expressions (36) and (37) are inversed because the sign of the output of reference fitters 151 and 159 are inversed.

Error signal e(n) is generated by subtractor 207.

A coefficient update operating portion 221 receives error signal e(n) and input signal (white noise) x(n) to adjust the filter coefficients of all zero filter 218 according to the expression (56). A coefficient update operating portion 230 receives error signal e(n) and an internal signal $g_{m-1}(n-1)$ of all pole filter 225 to adjust the filter coefficient $C_m(n)$ of all pole filter 225 according to the expression (57).

When the system identification filter shown in FIG. 10 is used, the system identification filter is applied to filters 151 and 159 shown in FIGS. 5 and 8.

Also upon system identification, the filter coefficient $C_m(n)$ of lattice-type all pole filter 225 is controlled such that its absolute value is made smaller than one. The stability of the filter upon system identification is guaranteed.

Figure 11:
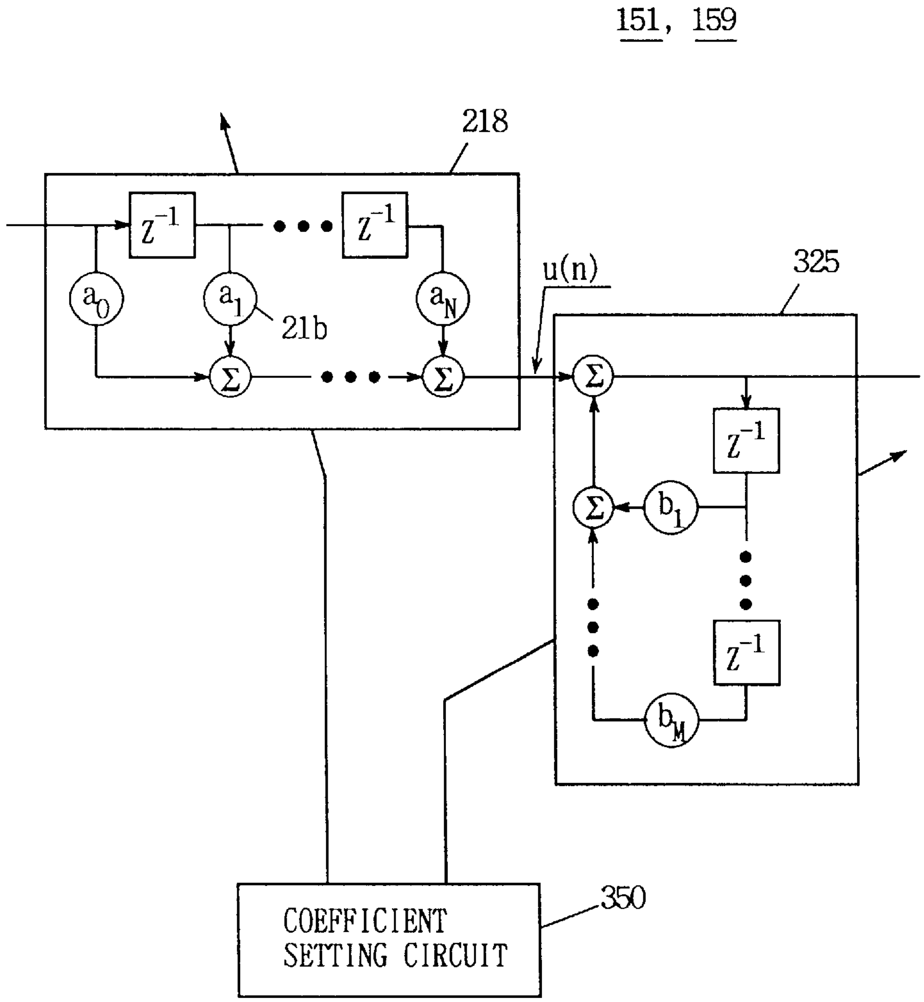
FIG. 11 shows a configuration of a filter obtained by equivalent conversion of the system identification filter shown in FIG. 10.

FIG. 11 is a diagram showing a configuration of a system identification filter according to the present invention. The filter shown in FIG. 11 includes a non-recursive all zero filter 218, and a recursive all pole filter 325 cascaded to non-recursive all zero filter 218. The filter shown in FIG. 11 configures a direct form IIR filter, and is applied to reference filters 151 and 159 shown in FIGS. 5 and 8. Filters 218 and 325 have their filter coefficients $a_i$, $C_m$ set through a coefficient setting circuit 350. The filter coefficient $C_m$ is converted into the coefficient $b_j$.

Figure 12:
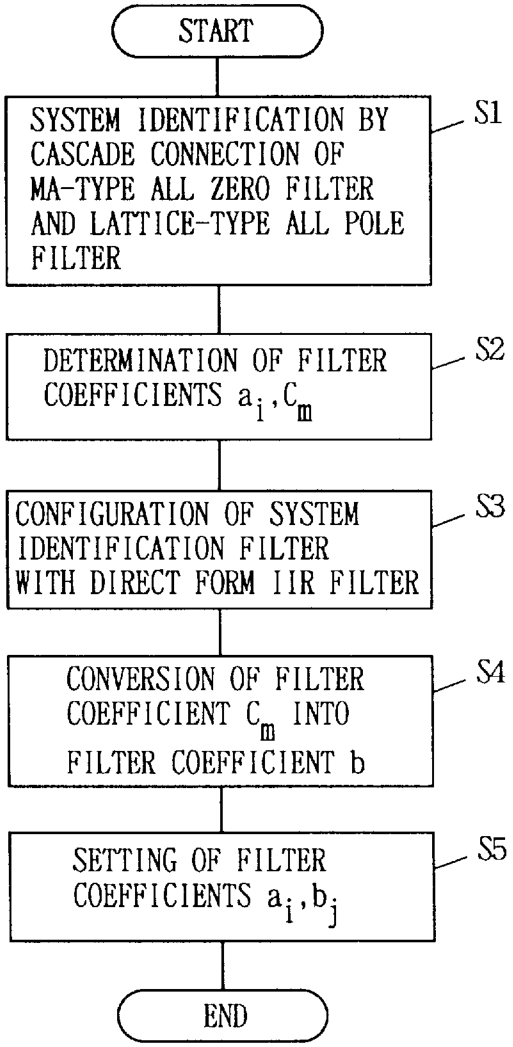
FIG. 12 is a flow diagram showing operation for generating the filter shown in FIG. 11.

The converting operation will be described with reference to a flow chart shown in FIG. 12.

After establishment of the identification object system, system identification operation is carried out using an IIR filter including the lattice-type all pole filter shown in FIG. 10 (step S1). The filter coefficients $a_i$, $C_m$ are updated adaptively upon the identification operation.

Based on the conditions that error signal $e^2(n)$ takes a predetermined value $\epsilon$ or less for a predetermined time period, the amount of change of the filter coefficients $a_i$, $C_m$ takes a predetermined value or less, it is determined that the filter coefficients are converged, and the system is identified (step S2). This determination establishes the filter coefficients $a_i$, $C_m$.

Then, the direct form IIR filter shown in FIG. 11 is prepared as a reference filter (step S3). Actually, the direct form IIR filter is incorporated in an active controller subjected to practical use.

The determined filter coefficient $C_m$ is converted into the filter coefficient of the all pole filter shown in FIG. 11. Levinson-Durbin's recurrence expression represented by the following expression, for example, is used for this conversion:

$$b_j(m+1)=b_j(m)+C_{m+1}\cdot b_{m-j+1}(m) \quad (58)$$

for j=0, 1, . . . M
where $$b_0(m)=1 \text{ for } m\neq 0,\ b_0(m)=0 \text{ for } m=0, \text{ and } C_0=1$$

$b_j(M)$ obtained through the recurrent relations with m changed from 0 to M−1 indicates a filter coefficient corresponding to the coefficient $C_m$. Here, upon application to the all pole filter 325, the sign of $b_j(M)$ is inverted, and $-b_j(M)$ is employed.

As a result, a direct form all pole filter having the same filter characteristic as the lattice-type all pole filter can be obtained.

After conversion into the coefficient $b_j$, filter coefficients $a_i$, $b_j$ are set to filters 218 and 325 through a coefficient setting circuit 350 shown in FIG. 11 (step S5). Cascade connection of an FIR filter (MA type all zero filter) and a lattice-type all pole filter is equivalently converted into a direct form IIR filter. The number of multiplying circuits of all pole filter 325 is half the number of those of all pole filter 225. The number of product sum operations is reduced, implementing high speed operation as well as reduction of controller size.

Figure 3:
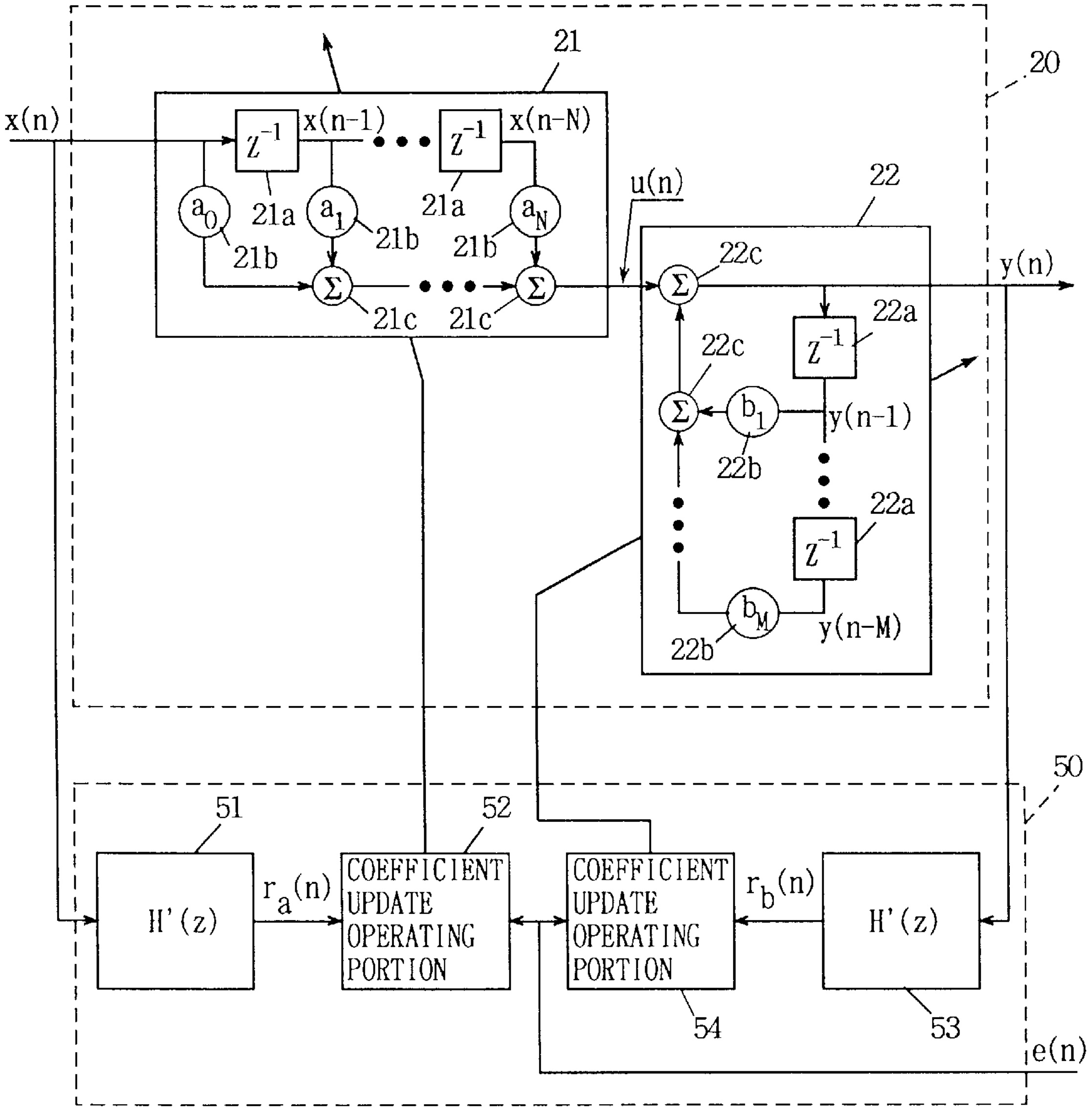
F I G. 3 PRIOR ART
FIG. 3 shows a specific configuration of a signal processing portion and an adapting portion shown in FIG. 2.
Figure 4:
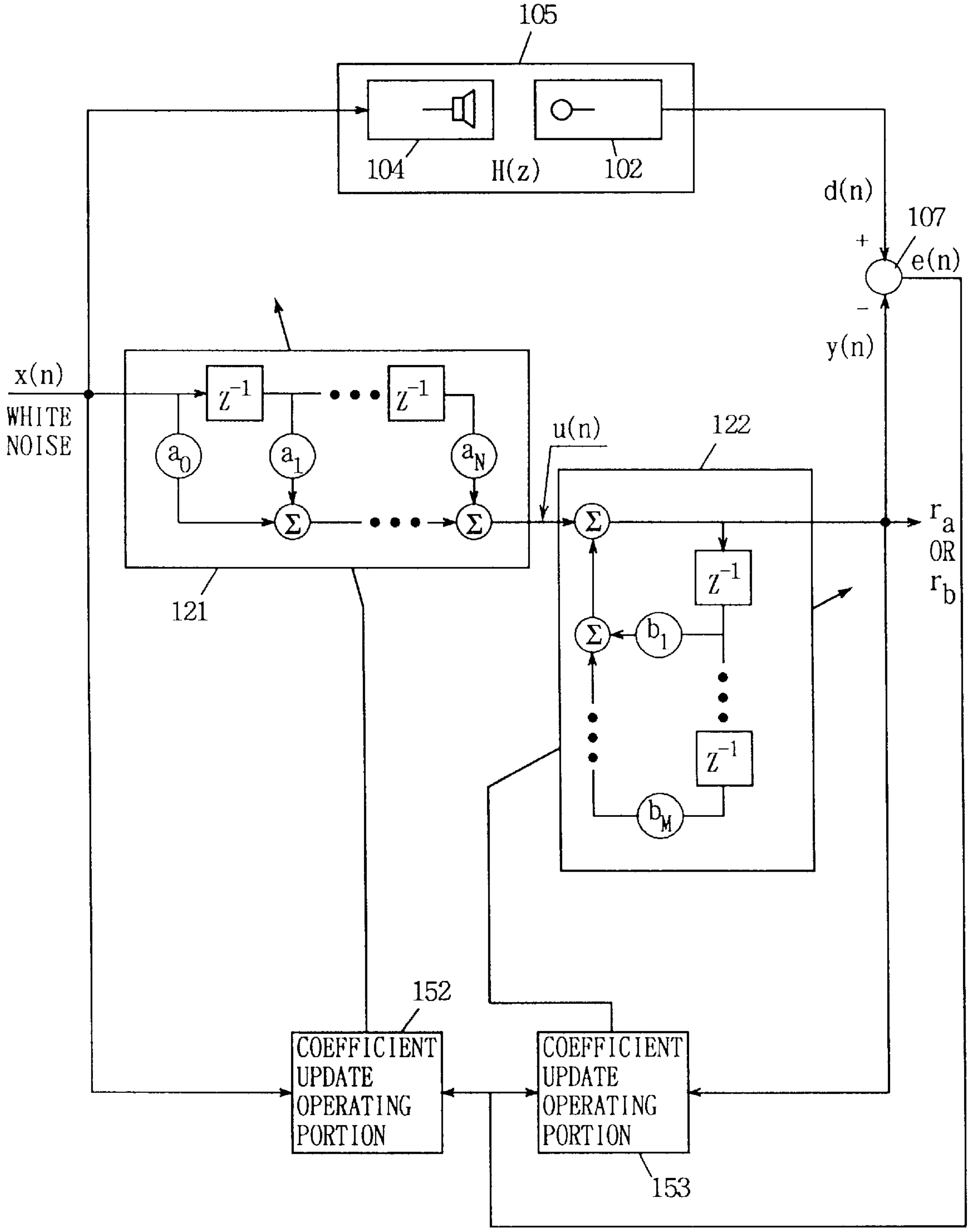
F I G. 4 PRIOR ART
FIG. 4 shows a configuration of a system identification filter shown in FIG. 3.

It should be noted that equivalent conversion of the system identification filter can also be applied to the conventional configuration shown in FIG. 3.

Figure 13:
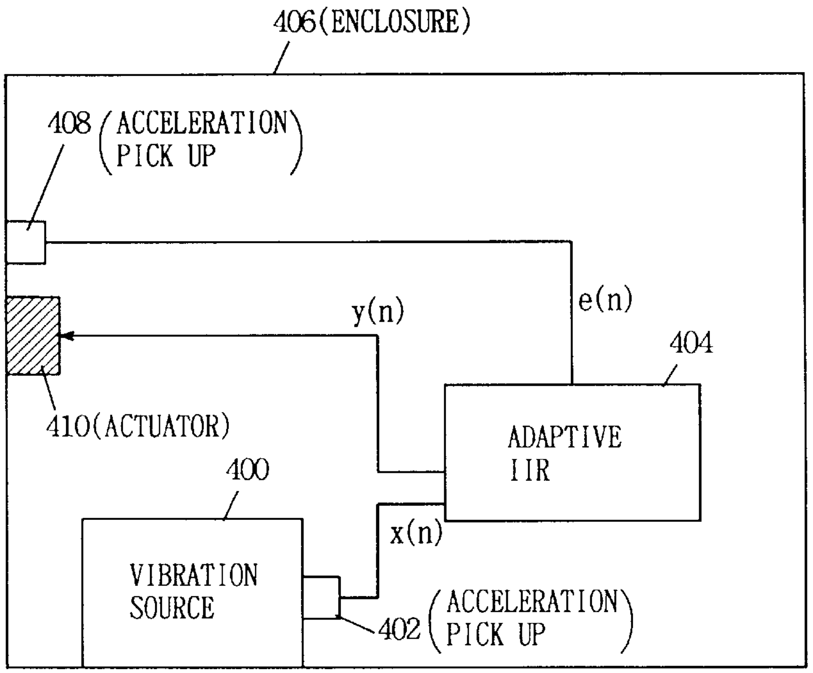
FIG. 13 shows another application of the present invention.
Figure 14:
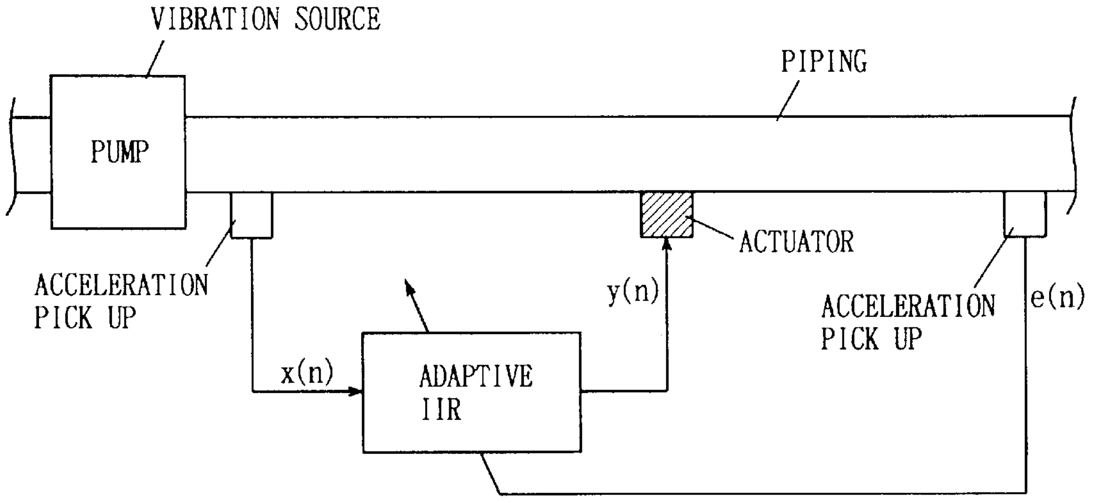
FIG. 14 shows still another application of the present invention.

As shown in FIGS. 13 and 14, by replacing microphones 1 and 2, respectively with an acceleration pickup and an actuator, an active vibration controller can be implemented.

In FIG. 13, vibration from a vibration source 400 is detected by an acceleration pickup 402, and applied to an adaptive IIR filter 404. Vibration of an enclosure 406 is detected by an acceleration pickup 408 to generate an error signal e(n) and to apply the same to adaptive IIR filter 404. Adaptive IIR filter 404 includes the above-described configuration of the present invention. Adaptive IIR filter 404 generates the signal y(n) from the signals x(n) and e(n) to apply the same to an actuator 410. Actuator 410 suppresses vibration from vibration source 402 by application of vibration.

In FIG. 14, a supply/discharge pump attached to a piping acts as a vibration source, and generates vibration in the piping. By an acceleration pickup in the vicinity of the pump, vibration on the piping is detected. By another acceleration pickup arranged apart from the pump, vibration on the piping is detected for generation of an error signal. The signal from the acceleration pickup is processed by the adaptive IIR filter according to the present invention. The actuator is driven according to the process result. Propagation of vibration from the pump through the piping is suppressed.

It should be noted that the present invention can be applied to an echo canceler and an adaptive equalizer as well as to a noise controller and a vibration controller. The present invention can be further applied to active control in general.

As described above, according to the present invention, even if disturbance or the like is generated in the adapting procedure of the filter coefficients, the stability of the filter can be reliably guaranteed.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An active controller, comprising:

detecting means for detecting an amount of a physical phenomena and generating a detect signal corresponding to the detected amount of the physical phenomena;

signal processing means for applying a predetermined processing to said detect signal and generating a control signal, said signal processing means having a non-recursive all zero digital filter receiving said detect signal for carrying out a first filtering process, and a lattice-type multi-stage all pole digital filter, receiving an output signal from said non-recursive all zero digital filter after the first filtering process, for carrying out a second filtering process on the output signal to generate said control signal;

output means for converting said control signal from said signal processing means into an amount of the physical phenomena for output;

error signal generating means, coupled to receive the amount of the physical phenomena provided from said output means, for generating an error signal indicative of a difference between a desired amount of the physical phenomena and the received amount of the physical phenomena; and adapting means for adjusting filtering characteristics of said non-recursive all zero digital filter and said lattice-type multi-stage all pole digital filter so that a magnitude of said error signal becomes minimum, according to said detect signal and said error signal, said adapting means including means coupled to receive said error signal and an interference signal which is indicative of an estimation of both a characteristic of an error propagation path and said output signal applied to said lattice-type multi-stage all pole digital filter, for adapting the filter characteristics of said lattice-type multi-stage all pole digital filter.

2. The active controller as recited in claim 1, wherein the amount of the physical phenomena is an amplitude of an acoustic wave.

3. The active controller as recited in claim 1, wherein said lattice-type multi-stage all pole digital filter comprises:

a forward path from an input node receiving the output signal of said non-recursive all zero digital filter toward an output node providing said control signal; and a backward path from said output node toward said input node, each stage of said lattice-type multi-stage all pole digital filter including a subtractor receiving a forward signal on said forward path from a preceding stage at a positive input, a first multiplier multiplying an output signal of said subtractor by a filter coefficient, a delay element delaying a backward signal on said backward path from a succeeding stage, a second multiplier multiplying an output signal of said delay element by said filter coefficient and applying the multiplication result to a negative input of said subtractor, and an adder adding output signals of said first multiplier and said delay element, said subtractor providing a forward signal onto said forward path and said adder providing a backward signal onto said backward path.

4. The active controller as recited in claim 3, wherein said adapting means comprises a plurality of adapting portions provided corresponding to each stage of said lattice-type multi-stage all pole digital filter, each of said plurality of adapting portions comprising:

product means for multiplying said error signal and a delayed backward signal applied through said backward path at a corresponding stage;

change amount calculating means for finding an amount of change of a filter coefficient at the corresponding stage according to an output signal of said product means; and determination means for determining a post-updated filter coefficient for said corresponding stage according to said amount of change.

5. The active controller as recited in claim 4, wherein said determination means comprises:

operating means for providing a first filter coefficient by arithmetic operation between said amount of change and a pre-updated filter coefficient at said corresponding stage;

determining means for determining whether said first filter coefficient is between a predetermined upper limit value and a predetermined lower limit value, said predetermined upper limit value and said predetermined lower limit value both having respective absolute values set smaller than one; and selecting means for selecting one of said first filter coefficient, said predetermined upper limit value and said predetermined lower limit value according to an output signal of said determining means as a selected output and providing the selected output as said post-updated filter coefficient.

6. The active controller as recited in claim 5, wherein said selecting means selects as said selected output (a) said first filter coefficient, (b) said predetermined upper limit value, and (c) said predetermined lower limit value when said determining means determines that (i) said first filter coefficient is between said predetermined upper limit value and said predetermined lower limit value, (ii) said first filter coefficient is at least said predetermined upper limit value, and (iii) said first filter coefficient is at most said predetermined lower limit value, respectively.

7. The active controller as recited in claim 1, wherein each stage of said lattice-type multi-stage all pole digital filter has a filter coefficient, and said adapting means includes updating means for updating said filter coefficients according to said error signal and said detect signal, said updating means including means for clipping a post-updated filter coefficient by a predetermined value having an absolute value less than one, thereby making all the absolute values of said post-updated filter coefficients less than one.

8. The active controller as recited in claim 1, wherein said adapting means comprises;

a reference filter filtering said detect signal according to a predetermined transfer characteristic to generate a reference signal; and updating means for adjusting a filter coefficient of said non-recursive all zero digital filter according to the reference signal from said reference filter and said error signal, said reference filter includes a second non-recursive all zero digital filter receiving said detect signal and a second lattice-type multi-stage all pole digital filter cascaded to said second non-recursive all zero digital filter.

9. The active controller as recited in claim 1, wherein said adapting portion comprises:

a reference filter filtering said detect signal according to a predetermined transfer characteristic to generate a reference detect signal;

a first update filter having a configuration identical to that of said non-recursive all pole digital filter and filtering an output signal of said reference detect signal;

a second update filter having a configuration identical to said lattice-type multi-stage all pole digital filter and cascaded to said first update filter; and coefficient updating means for determining update values of filter coefficients of said lattice-type multi-stage all pole digital filter according to said error signal and signals of corresponding stages of said second update filter.

10. The active controller as recited in claim 9, wherein said coefficient updating means comprises means for determining the update values of said filter coefficients according to a backward signal of corresponding stages of said second update filter and said error signal.

11. The active controller as recited in claim 9, wherein said coefficient updating means comprises means for determining the update values of said filter coefficients of said lattice-type multi-stage all pole digital filter according to both a forward signal and a backward signal of corresponding stages of said second update filter and said error signal.

12. The active controller as recited in claim 1, wherein said adapting means comprises:

a reference filter filtering an output signal of said non-recursive all zero digital filter according to a predetermined transfer characteristic;

an update filter having a configuration identical to that of said lattice-type multi-stage all pole digital filter and filtering an output signal of said reference filter; and coefficient updating means for determining an update value of a filter coefficient of each stage of said lattice-type multi-stage all pole digital filter according to said error signal and a signal of a corresponding stage of said update filter.

13. The active controller as recited in claim 12, wherein said coefficient updating means comprises means for determining the update value of the filter coefficient of each stage of said lattice-type multi-stage all pole digital filter according to a product of said error signal and a backward signal of the corresponding stage of said update filter.

14. The active controller as recited in claim 12, wherein said coefficient updating means comprises means for determining the update value of the filter coefficient of each stage of said lattice-type multi-stage all pole digital filter according to said error signal, a forward signal and a backward signal of the corresponding stage of said update filter and a filter coefficient of said lattice-type multi-stage all pole digital filter.

15. The active controller as recited in claim 1, wherein said adapting means comprises:

a multi-stage reference filter having a configuration identical to that of said lattice-type multi-stage all pole digital filter and having a filter coefficient of each stage thereof copied from a filter coefficient of a corresponding stage of said lattice-type multi-stage all pole digital filter; and means for determining an amount of update of a filter coefficient $C_m$ (n) at time n of the m-th stage of said lattice-type multi-stage all pole digital filter based on said error signal and a signal of a corresponding stage of said multi-stage reference filter such that $$C_m(n)=2\cdot\nu\cdot e(n)\cdot g^*_{m-1}(n-1)$$

where n represents time, ν represents a predetermined parameter, e(n) represents said error signal at time n, and $g_{m-}1$ * (n−1) represents a backward signal applied to the m-th stage of said multi-stage reference filter at time (n−1).

16. The active controller as recited in claim 1, wherein said adapting means comprises:

a multi-stage reference filter having a configuration identical to that of said lattice-type multi-stage all pole digital filter and having a filter coefficient of each stage thereof copied from a filter coefficient of a corresponding stage of said lattice-type multi-stage all pole digital filter; and means for determining an amount of update of a filter coefficient $C_m(n)$ at time n of the m-th stage of said lattice-type multi-stage all pole digital filter based on said error signal and signals of a corresponding stage of said multi-stage reference filter such that $$\underline{C_m(n) = 2} \cdot \nu \cdot e(n) \cdot \{g^*_{m-1}(n-1) + C_{m+1}(n)\psi_m(n) - g^*_{m-1}(n-2) \cdot \phi_{m-1}(n)\};$$

$$\psi_m(n) = 2 \cdot f^*_{m-1}(n-1) - f^*_m(n-1),$$

$$\phi_m(n) = C_{m+1}(n) \cdot C_m(n-1) + \phi_{m-1}(n)$$

where ν represents a predetermined value, $g_m$*(n) represents a backward signal provided from the m-th stage of said multi-stage reference filter at time n, and $f_m$*(n) represents a forward signal provided from the (m+1)-th stage of said multi-stage reference filter at time n.

17. The active controller as recited in claim 8, wherein said reference filter comprises a direct form IIR digital filter equivalent to an IIR filter including a non-recursive all zero digital filter and a lattice-type multi-stage all pole digital filter cascaded to the non-recursive all zero digital filter of the IIR filter, filter coefficients of an all pole digital filter of said direct form IIR digital filter being determined by equivalent conversion of filter coefficients of the lattice-type multi-stage all pole digital filter of the IIR filter.

18. The active controller as recited in claim 12, wherein said reference filter comprises a direct form IIR digital filter equivalent to an IIR filter including a non-recursive all zero digital filter and a lattice-type multi-stage all pole digital filter cascaded to the non-recursive all zero digital filter of the IIR filter, filter coefficients of an all pole digital filter of said direct form IIR digital filter being determined by equivalent conversion of filter coefficients of the lattice-type multi-stage all pole digital filter of the IIR filter.

19. A system identification apparatus identifying a transfer characteristic of a system generating a desired response value from an input amount of a physical phenomena, comprising:

a non-recursive all zero digital filter filtering said input amount of the physical phenomena; and a non-lattice recursive type all pole digital filter receiving an output signal of said non-recursive all zero digital filter and filter processing the output signal, a combination of said non-recursive all zero digital filter and said non-lattice recursive type all pole digital filter configuring a direct form IIR digital filter, filter coefficients of said non-lattice recursive type all pole digital filter being determined by equivalent conversion of filter coefficients of a lattice-type multi-stage all pole digital filter after identification of a transfer characteristic of the system by an IIR filter formed of said non-recursive all zero digital filter and said lattice-type multi-stage all pole digital filter cascaded to said non-recursive all zero digital filter.

20. A method of configuring a system identification apparatus identifying a transfer characteristic of a system generating a desired response value from an input amount of a physical phenomena, comprising the steps of:

(a) filtering said input amount of the physical phenomena to generate an output signal using a main circuit formed of a cascade connection of a non-recursive all zero digital filter and a lattice-type multi-stage all pole digital filter;

(b) generating an error signal indicating a difference between a desired response for said input amount of the physical phenomena from said system and said output signal;

(c) updating a filter coefficient of said main circuit so that said error signal becomes minimum;

(d) repeating said steps (a), (b), and (c) for identifying the transfer characteristic of the system to determine a filter coefficient of a filter of said main circuit; and (e) equivalently converting said main circuit into a direct form IIR digital filter formed of the non-recursive all zero digital filter and a non-lattice recursive type all pole digital filter.

21. The method of configuring a system identification apparatus as recited in claim 20, wherein said step (e) of equivalently converting comprises equivalently converting determined filter coefficients of said lattice-type multi-stage all pole digital filter into filter coefficients of the non-lattice recursive type all pole digital filter of said direct form IIR digital filter.

* * * * *